United States Patent
Sherman et al.

(10) Patent No.: US 6,821,281 B2
(45) Date of Patent: *Nov. 23, 2004

(54) MICROSTRUCTURES FOR TREATING AND CONDITIONING SKIN

(75) Inventors: Faiz Feisal Sherman, West Chester, OH (US); Vladimir Gartstein, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 273 days.

This patent is subject to a terminal disclaimer.

(21) Appl. No.: 09/952,403

(22) Filed: Sep. 14, 2001

(65) Prior Publication Data

US 2002/0045907 A1 Apr. 18, 2002

Related U.S. Application Data

(60) Provisional application No. 60/240,730, filed on Oct. 16, 2000, and provisional application No. 60/240,787, filed on Oct. 16, 2000.

(51) Int. Cl.[7] .................................................. A61B 17/50
(52) U.S. Cl. .......................................... 606/131; 606/35
(58) Field of Search ................................ 606/131, 201, 606/204, 204.35, 35; 433/88; 600/556

(56) References Cited

U.S. PATENT DOCUMENTS

| 3,918,449 A | 11/1975 | Pistor |
| 3,964,482 A | 6/1976 | Gerstel et al. |
| 4,180,232 A | 12/1979 | Hardigg |

(List continued on next page.)

FOREIGN PATENT DOCUMENTS

| DE | 2319591 | 11/1974 |
| DE | 196 24 578 A1 | 1/1998 |
| EP | 0 312 662 A1 | 4/1989 |

(List continued on next page.)

OTHER PUBLICATIONS

McAllister, H., "Micromachined Microneedles for Transdermal Drug Delivery", Allen & Prausnitz, Georgia Institute of Technology, Atlanta, GA.

Sebastian, H. et al., "Microfabricated Microneedles: A Novel Approach to Transdermal Drug Delivery", Journal of Pharmaceutical Sciences, Aug., 1998, pp. 922–925, vol. 87, No. 8, Atlanta, GA.

Chun, K. et al., An Array of Hollow Microcapillaries for the Controlled Injection of Genetic Materials into Animal/Plat Cells, The University of Tokyo.

Wouters, S. et al., "Microelectrochemical Systems for Drug Delivery", Electrochimica ACTA., 1997, pp. 3385–3390, vol. 42, Nos. 20–22.

(List continued on next page.)

Primary Examiner—Kevin T. Truong
Assistant Examiner—Victor Nguyen
(74) Attorney, Agent, or Firm—Larry L. Huston; Bart S. Hersko; Leonard W. Lewis

(57) ABSTRACT

An improved method and apparatus is provided as a system to enhance skin appearance and health, in which skin is cleaned (or exfoliated) and conditioned by use of microelements affixed to a base element or hand-held patch. The dimensions of the microelements are controlled so as to remove a certain number of layers of skin cells and to accumulate those skin cells, along with other foreign substances, into areas between the microelements. In addition, a conditioning compound or therapeutic active can be applied to the exfoliated skin to enhance the skin. Moreover, the amount of accumulated skin cells represents a self-limiting maximum quantity that cannot be substantially exceeded regardless of the number of attempts by a user to re-use the microstructure apparatus.

5 Claims, 20 Drawing Sheets

U.S. PATENT DOCUMENTS

| | | | |
|---|---|---|---|
| 4,381,963 A | 5/1983 | Goldstein et al. | |
| 4,585,991 A | 4/1986 | Reid et al. | |
| 4,784,737 A | 11/1988 | Ray et al. | |
| 4,837,049 A | 6/1989 | Byers et al. | |
| 5,134,079 A | 7/1992 | Cusack et al. | |
| 5,156,591 A | 10/1992 | Gross et al. | |
| 5,158,073 A | 10/1992 | Bukowski | |
| 5,162,043 A | 11/1992 | Lew et al. | |
| 5,198,192 A | 3/1993 | Saito et al. | |
| 5,215,088 A | 6/1993 | Normann et al. | |
| 5,250,023 A | 10/1993 | Lee et al. | |
| 5,250,067 A * | 10/1993 | Gelfer et al. | 606/189 |
| 5,256,360 A | 10/1993 | Li | |
| 5,279,544 A | 1/1994 | Gross et al. | |
| 5,318,557 A | 6/1994 | Gross | |
| 5,362,307 A | 11/1994 | Guy et al. | |
| 5,383,512 A | 1/1995 | Jarvis | |
| 5,498,235 A | 3/1996 | Flower | |
| 5,512,219 A | 4/1996 | Rowland et al. | |
| 5,527,288 A | 6/1996 | Gross et al. | |
| 5,551,953 A | 9/1996 | Lattin et al. | |
| 5,591,123 A | 1/1997 | Sibalis et al. | |
| 5,591,139 A | 1/1997 | Lin et al. | |
| 5,611,806 A * | 3/1997 | Jang | 606/167 |
| 5,645,977 A | 7/1997 | Wu et al. | |
| 5,658,515 A | 8/1997 | Lee et al. | |
| 5,676,850 A | 10/1997 | Reed et al. | |
| 5,681,580 A | 10/1997 | Jang et al. | |
| 5,704,520 A | 1/1998 | Gross | |
| 5,711,761 A | 1/1998 | Untereker et al. | |
| 5,728,089 A | 3/1998 | Lal et al. | |
| 5,730,714 A | 3/1998 | Guy et al. | |
| 5,735,273 A | 4/1998 | Kurnik et al. | |
| 5,771,890 A | 6/1998 | Tamada | |
| 5,800,420 A | 9/1998 | Gross et al. | |
| 5,807,375 A | 9/1998 | Gross et al. | |
| 5,814,020 A | 9/1998 | Gross | |
| 5,820,622 A | 10/1998 | Gross et al. | |
| 5,827,183 A | 10/1998 | Kurnik et al. | |
| 5,848,985 A | 12/1998 | Muroki | |
| 5,848,990 A | 12/1998 | Cirelli et al. | |
| 5,848,991 A | 12/1998 | Gross et al. | |
| 5,855,801 A | 1/1999 | Lin et al. | |
| 5,879,326 A | 3/1999 | Godshall et al. | |
| 5,938,684 A * | 8/1999 | Lynch et al. | 606/204 |
| 5,964,729 A | 10/1999 | Choi et al. | |
| 6,023,629 A | 2/2000 | Tamada | |
| 6,036,659 A | 3/2000 | Ray et al. | |
| 6,038,465 A | 3/2000 | Melton, Jr. | |
| 6,047,208 A | 4/2000 | Flower | |
| 6,083,196 A | 7/2000 | Trautman et al. | |
| 6,091,975 A | 7/2000 | Daddona et al. | |
| 6,106,751 A | 8/2000 | Talbot et al. | |
| 6,129,696 A | 10/2000 | Sibalis | |
| 6,132,755 A | 10/2000 | Eicher et al. | |
| 6,219,574 B1 | 4/2001 | Cormier et al. | |
| 6,256,533 B1 | 7/2001 | Yuzhakov et al. | |
| 6,312,612 B1 * | 11/2001 | Sherman et al. | 216/2 |
| 6,334,856 B1 | 1/2002 | Allen et al. | |
| 6,375,627 B1 | 4/2002 | Mauze et al. | |
| 6,379,324 B1 * | 4/2002 | Gartstein et al. | 604/22 |
| 6,440,096 B1 | 8/2002 | Lastovich et al. | |
| 6,451,240 B1 | 9/2002 | Sherman et al. | |
| 6,471,903 B2 | 10/2002 | Sherman et al. | |
| 6,476,288 B1 * | 11/2002 | VanRijswijck et al. | 604/364 |
| 6,494,830 B1 | 12/2002 | Wessel | |
| 6,533,884 B1 | 3/2003 | Mallik | |
| 6,565,532 B1 * | 5/2003 | Yuzhakov et al. | 604/142 |
| 6,591,124 B2 | 7/2003 | Sherman et al. | |
| 2001/0023324 A1 | 9/2001 | Pronovost et al. | |
| 2002/0006355 A1 | 1/2002 | Whitson | |
| 2002/0045859 A1 | 4/2002 | Gartstein et al. | |
| 2002/0045907 A1 | 4/2002 | Sherman et al. | |
| 2002/0133129 A1 | 9/2002 | Arias et al. | |
| 2002/0177858 A1 | 11/2002 | Sherman et al. | |

FOREIGN PATENT DOCUMENTS

| | | |
|---|---|---|
| EP | 0 407 063 A1 | 1/1991 |
| EP | 0 796 128 B1 | 11/1995 |
| EP | 1 086 719 A1 | 3/2001 |
| EP | 1 174 078 A2 | 1/2002 |
| FR | 2535602 A1 | 11/1984 |
| GB | 2221394 A | 2/1990 |
| JP | 09-051878 | 2/1997 |
| SU | 1 667 864 | 7/1991 |
| WO | WO 93/17754 A1 | 9/1993 |
| WO | WO 94/23777 A1 | 10/1994 |
| WO | WO 96/00109 A1 | 1/1996 |
| WO | WO 96/37155 A1 | 11/1996 |
| WO | WO 96/37256 A1 | 11/1996 |
| WO | WO 97/03718 A1 | 2/1997 |
| WO | WO 97/48440 A1 | 12/1997 |
| WO | WO 97/48441 A1 | 12/1997 |
| WO | WO 97/48442 A1 | 12/1997 |
| WO | WO 98/00193 A1 | 1/1998 |
| WO | WO 99/00155 A1 | 1/1999 |
| WO | WO 99/29298 A2 | 6/1999 |
| WO | WO 99/29364 A1 | 6/1999 |
| WO | WO 99/29365 A1 | 6/1999 |
| WO | WO 99/64580 A1 | 12/1999 |
| WO | WO 00/05166 A1 | 2/2000 |
| WO | WO 00/35530 A1 | 6/2000 |
| WO | WO 00/74763 A2 | 12/2000 |
| WO | WO 00/74765 A1 | 12/2000 |
| WO | WO 00/74766 A1 | 12/2000 |
| WO | WO 02/07813 A1 | 1/2002 |
| WO | WO 02/72189 A2 | 9/2002 |
| WO | WO 03/24290 A1 | 3/2003 |
| WO | WO 03/24518 A2 | 3/2003 |

OTHER PUBLICATIONS

Prausnitz, M. R., et al., "Transdermal Delivery of Macromolecules: Recent Advances by Modification of Skin's Barrier Properties", Therapeutic Protein and Peptide Formulation and Delivery, pp. 124–153, Chapter 8, ACS Symposium Series 675, Georgia Institute of Technology.

Prausnitz, M. R., et al., Transdermal Transport Efficiency During Skin Electroporation and Iontophoresis, Journal of Controlled Release 38, 1996, pp. 205–217, Massachusetts Institute of Technology, Cambridge, MA.

Papautsky, I. E., et al., "Micromachined Pipette Arrays (MPA)", pp. 2281–2284, Proceedings —19$^{th}$ International Conference —IEEE/EMBS Oct. 30–Nov. 2, 1997, Chicago, IL.

* cited by examiner

US 6,821,281 B2

MICROSTRUCTURES FOR TREATING AND CONDITIONING SKIN

CROSS REFERENCE

This application claims the benefit of U.S. Provisional Application Nos. 60/240,730 and 60/240,787 both filed on Oct. 16, 2000.

TECHNICAL FIELD

The present invention relates generally to systems for treating and conditioning skin and is particularly directed to an article of manufacture used to perform one or more functions such as enhancing skin, removing dead skin cells, removing accumulated make-up and cosmetics, extracting skin constituencies, depositing skin enhancing compositions, and improving skin appearance. The invention is specifically disclosed as a planar array of microelements that delivers an adjunct skin enhancement composition from at least one reservoir attached thereto, or the composition can be applied directly to skin and utilized therein in combination with the article of manufacture.

BACKGROUND OF THE INVENTION

Human skin is the largest organ. Skin and hair are the surfaces of the human body that are visible to others and the appearance of skin is important to good grooming and health. Human skin comprises several layers, the outermost is the stratum corneum, which comprises dead skin cells and makes up a substantial portion of the first protective barrier of the body. Most skin comprises a stratum corneum which is 15–20 layers of dead cells thick (about 10–20 microns in thickness). However, some "durable" skin layers, such as heels or calluses, can comprise a stratum corneum which is from 100–150 microns thick. On average, the skin naturally sheds at least one skin layer each day, and the first one to four layers of skin may be removed without affecting the protective nature of skin or the health thereof. In fact, removing up to four (4) layers of the stratum corneum may provide a skin surface area onto which make-up may be more uniformly applied and once applied has a more aesthetically pleasing appearance.

The removal of up to the first ten (10) layers of skin may also instigate resolution of and/or removal of unwanted comedones which themselves may be the result of skin pores being blocked by bacteria, dirt, dead cells, make-up, etc. The removal of skin layers in a safe and convenient manner can be indirectly accomplished in a limited manner by washing (or scrubbing) with an abrasive cloth, for example, a terry cloth sheet, but only skin cells which are about to shed are removed. However, make-up can be deposited into opened pores and if not thoroughly rinsed can leave the skin with an unwanted film of dirt, dead skin cells, oxidized oil.

There is therefore a long felt need for a system for providing enhanced skin health and appearance by helping to remove the outermost layer of human skin. There is also a need for a system which is capable of delivering to human skin one or more treatments which result in a smooth skin condition which facilitates the application of appearance enhancement compositions, cosmetics, and other materials or actives.

In conventional skin treatment or preparation methodologies, the skin cells scraped loose tend to become airborne when a mechanical scrubber is used. These airborne skin cells are distasteful at best, and could represent some type of health hazard in certain situations. In view of this situation, there further is a need to prepare skin in a manner such that most or all of the removed or "loose" skin cells do not become airborne.

In conventional skin treatment or preparation methodologies, the user has great control over the quantity of skin cells that are scraped loose from the skin, simply by rubbing harder, or by rubbing a larger (or smaller) number of strokes. This can be an undesirable situation, since the person may possibly injure himself or herself by being too vigorous, or since the person may achieve nothing by not being vigorous enough. It would be a significant improvement to provide an article of manufacture that can essentially guarantee that a predetermined maximum quantity of skin cells will be removed by application of that article on skin, such that the article's use is essentially fool-proof by virtue of its effects being self-limiting, so that only a maximum amount of skin cells can be removed, regardless of the user's very vigorous attempts to continue the rubbing strokes.

SUMMARY OF THE INVENTION

Accordingly, it is an advantage of the present invention to provide a method and apparatus that can enhance the health and the appearance of human skin.

It is another advantage of the present invention to provide an article of manufacture to treat the surface of skin, which is capable of selectively modifying the skin surface and capable of discriminately removing differential amounts of the body's outer skin layer (the stratum corneum).

It is a further advantage of the present invention to provide articles of manufacture that are capable of removing not only unwanted layers of skin, but can also be fashioned in a manner to selectively remove body hair. At the same time the skin is being conditioned, the articles of manufacture can controllably deposit one or more skin care compositions thereto or provide a skin treatment.

It is still another advantage of the present invention to provide articles of manufacture which can deliver a metered amount of a composition, remove a specific number of cellular layers (e.g., skin layers), and the like; the articles of manufacture can also be made for any type of one-time treatment after which the individual article is disposed of.

Additional advantages and other novel features of the invention will be set forth in part in the description that follows and in part will become apparent to those skilled in the art upon examination of the following or may be learned with the practice of the invention.

To achieve the foregoing and other advantages, and in accordance with one aspect of the present invention, a method for removing cells from skin is provide, in which the method comprises the steps of: (1) providing a microstructure having a substrate and a plurality of microelements; (2) placing the microstructure on skin then rubbing the microstructure against the skin, thereby scraping and accumulating skin cells on the substrate in areas between the plurality of microelements; and (3) withdrawing the microstructure from the skin, and thereby removing a large majority of the skin cells that have accumulated upon the substrate.

In accordance with another aspect of the present invention, a microstructure apparatus is provided, which comprises: (1) a substrate and a plurality of microelements affixed upon a first surface of the substrate; (2) the plurality of microelements being of a predetermined size and shape so as to scrape a substantially predetermined quantity of skin cells from skin when the microstructure apparatus is placed upon the skin and moved in at least one predetermined direction; and (3) the plurality of microelements being spaced-apart from one another upon the substrate by a predetermined distances so as to remove a large majority of the scraped skin cells when the microstructure apparatus is withdrawn from the skin.

The present invention relates further relates to embodiments of the article of manufacture which allows simultaneous delivery of a skin-enhancing composition in conjunction with removing one or more constituents of skin or modifying the skin surface for further treatment. Such a skin-enhancing composition could include both a biological active and a chemical active.

Still other advantages of the present invention will become apparent to those skilled in this art from the following description and drawings wherein there is described and shown a preferred embodiment of this invention in one of the best modes contemplated for carrying out the invention. As will be realized, the invention is capable of other different embodiments, and its several details are capable of modification in various, obvious aspects all without departing from the invention. Accordingly, the drawings and descriptions will be regarded as illustrative in nature and not as restrictive.

All percentages, ratios and proportions herein are by weight, unless otherwise specified. All temperatures are in degrees Celsius (° C.) unless otherwise specified. All documents cited are in relevant part, incorporated herein by reference.

BRIEF DESCRIPTION OF THE DRAWINGS

The accompanying drawings incorporated in and forming a part of the specification illustrate several aspects of the present invention, and together with the description and claims serve to explain the principles of the invention. In the drawings:

DETAILED DESCRIPTION OF THE INVENTION

Figure 1:
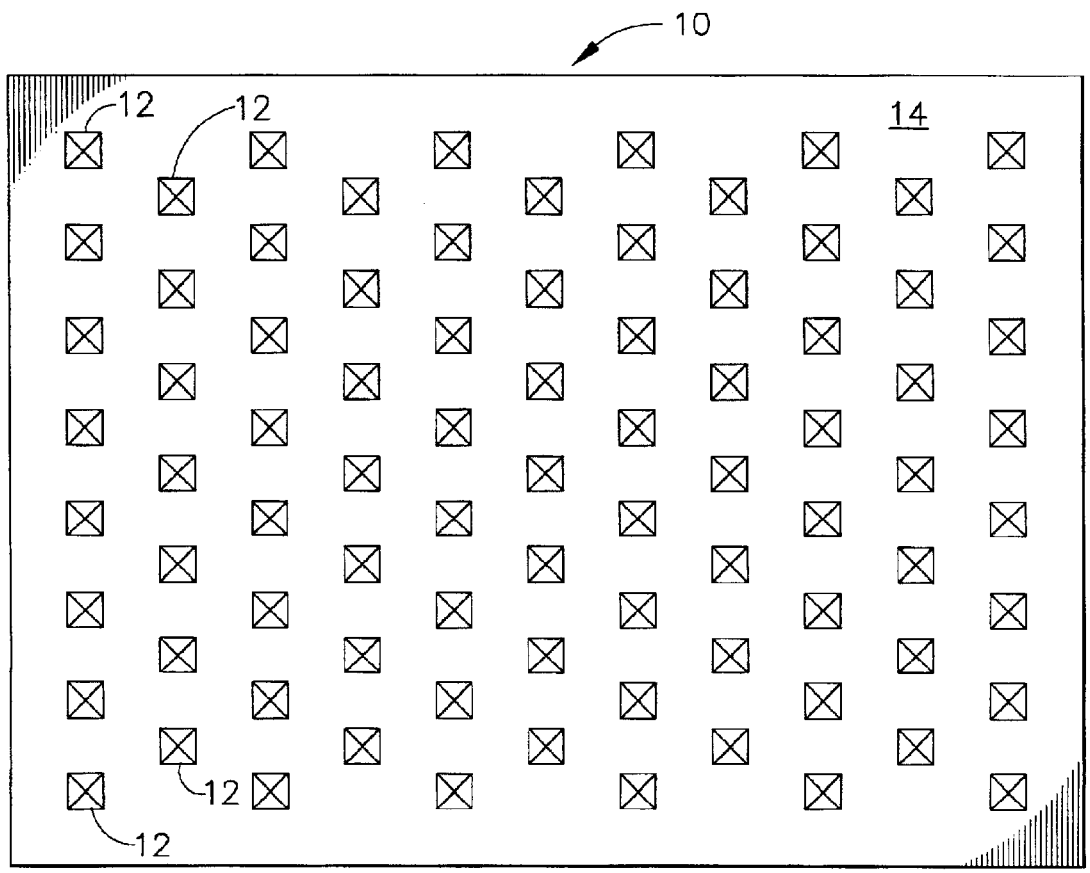
FIG. 1 is a plan view of an array of microelements that are pyramidal in shape, as constructed according to the principles of the present invention.

Reference will now be made in detail to the present preferred embodiment of the invention, an example of which is illustrated in the accompanying drawings, wherein like numerals indicate the same elements throughout the views.

The present invention relates to improving the health and condition, including the appearance, of human skin. The present invention comprises a system which utilizes an article of manufacture capable of selectively treating human skin and which can be modified depending upon the area of human skin which is to be treated, such as the face, hands, or feet; the type of treatment which is to be provided, such as skin refreshment; the type of adjunct compositions to be administered thereto, such as astringents, make-up, make-up remover, or at least one active or drug; or the respective frequency of use, as for example, daily in home use, or a single treatment by a skin care or medical professional in a clinic.

For the purposes of the present invention the term "skin enhancement treatment" is defined as "treatment of human skin with an article of manufacture as defined herein, wherein the surface of the skin is modified by controllably removing a selected number of skin layers or removing skin to a predetermined depth, and optionally, delivering to the skin which has been treated, a skin enhancing composition, and/or removal therefrom of any unwanted substances." Embodiments of the present invention are directed to a wide range of skin enhancements, each enhancement based upon the type, configuration, and material, which comprises the microelements described herein. In addition, to the effects produced by the selected microelement, the systems of the present invention optionally comprise a composition that provides skin conditioning benefits.

The stratum corneum of skin comprises layers of dead skin cells, which are part of the body's protective outer layer. This outermost layer of skin cells can have a nominal thickness of from about one hundred (100) microns to about 250 microns for thick, durable skin areas, such as calluses, whereas normal, "thin" skin may comprise from about ten to about fifteen microns (10–15) thickness for its stratum corneum. One aspect of the present invention relates to the removal of the outermost layers (e.g., from 1 to 4 layers) of the stratum corneum. The articles of manufacture described herein are capable of selectively removing a predetermined number of skin layers (also known as "exfoliation"). This is achieved by adjusting the configuration of the microelements and/or the distance from which the distal end of the microelements protrudes from a particular base element.

By adjusting the configuration of the microelements, not only is the depth of skin scraping action modulated, but also the type of scraping action (or "rubbing") can be adjusted. For example, the articles of manufacture of the present invention may have hollow or grooved microelements that can serve as passages through which a substance may flow. These passages allow for transport of a material to the skin, for example, an emollient, or, as in the case of removed cellular tissue, dirt, etc., a material from the skin or skin constituents.

As used herein, the term "rubbing" represents an action by which one of the microstructures of the present invention is placed upon skin and moved (or "scraped") along the surface of the skin. The rubbing action (or "scraping" action) can be achieved manually, or by using a device. In other words, the microstructure can be held by hand and manually rubbed against the skin, or the microstructure can be placed on a mechanical device that will, in turn, be used to move (or rub) the microstructure upon the surface of the skin.

Articles of Manufacture

The articles of manufacture of the present invention comprise a base element (or "substrate") onto which is affixed or deposed a plurality of microelements. The following is a description of the base element and corresponding microelements.

Base Element

The articles of manufacture of the present invention comprise at least one base element having a first side and a second side. Onto the first side are affixed the microelements as described hereinbelow. Aside from providing a template or base structure onto which the microelements are affixed, the second side, or reverse side, may in turn comprise a handle or other means by which the article of manufacture can be held. In another embodiment, a substance can be deposed upon the second side, which allows the user to grasp, hold, or otherwise control the motion of the article using only the fingertips. The use of a material to provide a tactile surface is especially compatible for embodiments wherein the base element comprises a thin, substantially flexible material, such as paper or polymeric sheets. One embodiment of the present invention includes base elements which comprise flexible sheets, and the thickness of the sheets is determined by the desired degree of flexibility. The flexible sheets are typically rigid enough to provide a template upon which the microelements can be affixed, but which are easily deformed to fit the contours of the skin surface.

The base elements of the present invention may have any shape or configuration. For example, one embodiment relates to circular base elements, while another embodiment relates to rectangular base elements having a width and a length. For such articles of manufacture that comprise microelements having a "microelement angle" less than 90° as defined hereinbelow, rectangular base elements will have a left edge and a right edge. The right edge of the base element is defined herein as the edge along the right side of the base element when the second side of the base element is facing down (away from the observer) and the first side is facing the observer. The left edge is oppositely defined herein.

In another embodiment of the present invention, the second side may have at least one reservoir (or chamber) attached thereto (or constructed therewith) which contains a flowable (or "fluidic") composition, or at least one reservoir or chamber for receiving material (e.g., hair, oils, skin cells) removed from skin. For embodiments of this type, it is an option to modify the base element to comprise a plurality of hollow elements, or to provide channels or pore openings along with solid microelements. Such hollow elements or channels would ostensibly provide a means for a deliverable material or removable material to flow from the first side of the base element to the second side, or vice versa. The hollow elements can also be in register with a hollow element, channel, hole, or other passageway which modifies the microelements as described hereinbelow in a manner that allows a flowable composition to be delivered from the reservoir through a hollow element in the base element, through a tube or channel of the microelement, and onto skin.

For purposes of the present invention, the terms "fluid" or "fluidic" have a meaning that includes flowable liquids, flowable gases, relatively low-viscosity creams, flowable solutions that may contain solid particles, and the like. A "fluidic compound" or "fluidic material" specifically includes such liquids, gases, and solutions; these compounds or materials may comprise at least one active, a drug, or a skin conditioner, or other useful composition of matter; alternatively, the term "fluidic compound" can represent at least two actives, drugs, or the like, including both a biological active and a chemical active (in a single fluidic compound).

Microelements

The articles of manufacture of the present invention further comprise a plurality of microelements, which are affixed to the first side or first surface of the base element. The "proximal end" of the microelement is defined herein as "the microelement end that is affixed to or in register with the base element." The "distal end" of the microelement is defined herein as "the microelement end which comes into contact with skin, and which is the opposite end of the microelement from the proximal end." The term "microelement" is defined herein as "an appendage for contacting skin which extends from the first side of the base element and is affixed thereto (or protrudes therefrom) at an attachment angle." The term "microelement" refers to the entire element which contacts the skin and includes not only the appendage itself, but the attachment angle, any hollow elements or grooves, the density of the microelements as measured in the number of appendages per square centimeter, and any predisposed skin enhancement composition.

The term "skin" is defined herein as "animal skin, including human skin, plant skin or surfaces, and even other biological structures that may not have a true "skin" organ, such as tissue samples of either plant or animal origin."

For the purposes of the present invention, the term "affixed" as it relates to attachment of the microelements to the base element is defined as "held permanently to the first side of the base element." Affixed microelements are neither removable nor detachable. The microelements of the present invention, as it relates to the term "affixed" can comprise any suitable embodiment. For example, the microelements and base element may comprise a single uniform composition or the microelements may be extruded from the material comprising the first side.

Alternatively, and in a separate embodiment, the microelements may be applied to the base element in a separate operation or manufacturing step, such as lamination to a non-woven substrate. Therefore, the microelements can be fashioned and applied in any manner the formulator desires which achieves the desired microelement density or configuration. Other suitable microelement configurations include those described in United States Patent Applications: U.S. Ser. Nos. 09/580,780, 09/580,819, and 09/579,798 all filed May 26, 2000; U.S. Ser. No. 09/614,321 filed Jul. 12, 2000 all of which are commonly-assigned to The Procter & Gamble Company, and which are incorporated herein by reference.

For the purposes of the present invention the term "microelement density" is defined herein as "the number of microelements per square centimeter of base element surface."

The appendages that comprise the microelements may be of any configuration that is capable of providing the desired skin enhancement. One embodiment of the present invention relates to a plurality of appendages in the form of regular conical appendages. Regular conical appendages have a circular proximal end and a pointed or rounded distal end. Another embodiment relates to inverted conical microelements, in which the appendages are conical appendages affixed to the base element at the tapered end and the circular base comprises the distal end. Rod-shaped appendages are circular or elliptical rods having a uniform circumference along the entire length. Planar appendages are cubes or cubic rectangles (or open boxes) wherein the length and width are uniform (but not necessarily equal to one another) throughout the height of the appendage and the distal end comprises a plane, such as a square, rectangle, or trapezoid, in which the plane is parallel to the base element or at an angle thereto. Wedge-shaped appendages have a rectangular proximal base that tapers to a line segment, which preferably has the same length as the length of the rectangular base. Some wedge-shaped appendages have an inverted appearance. Pyramidal appendages may comprise bases which have three or four sides at the proximal end base, and which taper to a point or rounded top at the distal end. Alternatively, the wedge-shaped appendages may have a triangular section removed therefrom that acts to facilitate the removal of skin hair follicles. The appendages of the present invention may also be coiled having any number of turns from the proximal end to the distal end.

For the purposes of the present invention the term "microelement angle" is defined as the "angle at which the appendage of the microelement protrudes from the base element." For example, a microelement, which is affixed perpendicular to the base element, has a microelement angle of 90°. The microelements of the present invention can be affixed to the base element at any angle from about 30° to about 90° (perpendicular). However, if the direction of use of the article of manufacture is not symmetrical, the microelements can be affixed to the base element at any angle from about 30° to about 150°. In addition, microelements which are not perpendicular to the base element may be angled toward any edge of a rectangular or square base element, or be perpendicular to the tangent of any point along the circumference of a circular base element.

The microelements of the present invention may also comprise hollow elements or contain grooves. Hollow elements are typically disposed along the longitudinal axis of the appendage portion of the microelement and are in register with a corresponding hollow element or passageway at the base element. Grooves or indented elements occur along the surface of an appendage and serve, like hollow elements, to move material toward the skin or remove material therefrom. For example, embodiments which provide a skin conditioning composition to the skin may use a series of hollow elements to deliver the composition from at least one reservoir to the skin. Or, natural facial oils may be carried away from the skin surface by capillary action though hollow elements or by inductive flow along grooves on the surface of the appendages.

The microelements of the present invention may range from absolute rigid (inflexible) to flexible. For the purposes of the present invention, the term "flexible" is defined herein as "during use against skin, the distal end of an appendage is bent or deformed up to 90° from the microelement angle as defined herein above." A perpendicular appendage which is bent 90° is therefore parallel with the base element. An appendage having a microelement angle of 45° can be deformed or bent to an angle of 135°.

The microelements of the present invention may have a protrusion distance of up to 150 microns from the surface of the base element. The term "protrusion distance" is defined herein as "the distance from distal end of the microelement along a line parallel to the base element." For perpendicular microelements the length of the appendage and the protrusion distance are equivalent. A microelement having a microelement angle, for example, of 30° will have a protrusion distance equal to one half the length of the appendage.

One embodiment of the present invention relates to microelements having a protrusion distance of about 1–100 microns. Another embodiment relates to protrusion distances of about 1–50 microns. Further embodiments encompass microelements wherein the appendages have protrusion distances from about one to about twenty (1–20) microns, whereas other embodiments include protrusion distances of from about five to about twenty (5–20) microns and from about four to about twenty (4–20) microns, as well as embodiments from about four to about ten microns (4–10). Other embodiments comprise no range of protrusion distances but have discreet distances such as, for example, a 4-micron embodiment, a 5-micron embodiment, or a 10-micron embodiment.

The microelements of the present invention may comprise an appendage, which has flexible elements and rigid elements, for example, an appendage which has a rigid portion extending from about the middle of the element to the proximal end and a flexible portion extending from about the middle of the element to the distal end. Articles of manufacture which are composites of several materials may comprise a thin flexible base element onto which are deposed rigid, inflexible microelements.

The articles of manufacture of the present invention may comprise a multitude of arrays, each array comprising the same or different types or sizes of microelements, in which the various attributes of the microelements, including microelement density, appendage type, microelement angle, hollow elements vs. solid elements with or without grooves, degree of flexibility, protrusion distance, etc. may vary from array to array or within a single particular array. For the purposes of the present invention the term "array" is defined as "multiple microelements in a pattern."

In some cases, certain array elements collectively may be separated from another array by a distance which is greater than the distance between the microelements which comprise the first array. In other cases, arrays may contain different types of microelements which all have the same spacings. The distance between microelements along the edge of two separate and distinct arrays may be greater than the distance between two microelements, which are members of the same array. Alternatively, several different microelement shapes or protrusion sizes may exist in a single array in which all individual elements are spaced-apart from one another in a consistent manner throughout the entire structure.

The microelements preferably have a length and shape that will tend to scrape skin cells (typically dead or loose skin cells) from the upper surface of the stratum corneum, while at the same time will not tend to penetrate entirely through the stratum corneum layer. The characteristic of the microelements to not cut or penetrate entirely through the stratum corneum is further enhanced by directing the user to move the "patch" or microstructure in only one direction (or in a single line that represents a back and forth direction), so that the "sharper" edges of the microelements do not tend to cut or plow into the skin upper layers; instead, these sharper edges merely assist in scraping away the skin cells. As will be seen in the drawings, some of the microelements have shapes that also assist in accumulating the skin cells (as well as other foreign substances found on the skin surface) once they have been scraped loose.

Referring now to the drawings, FIG. 1 illustrates a microstructure array generally designated by the reference numeral 10 containing multiple microelements 12 that are situated on a base or substrate 14. In FIG. 1, each "column" of microelements 10 is offset from the next, adjacent column of similar microelements. However, each of the columns could be made to be identical to one another, if desired, and the offset could be removed. Alternatively, there could be several columns with various offsets before the microelement pattern repeats, or the offsets could be substantially random so that there is no repetitive pattern.

Figure 2:
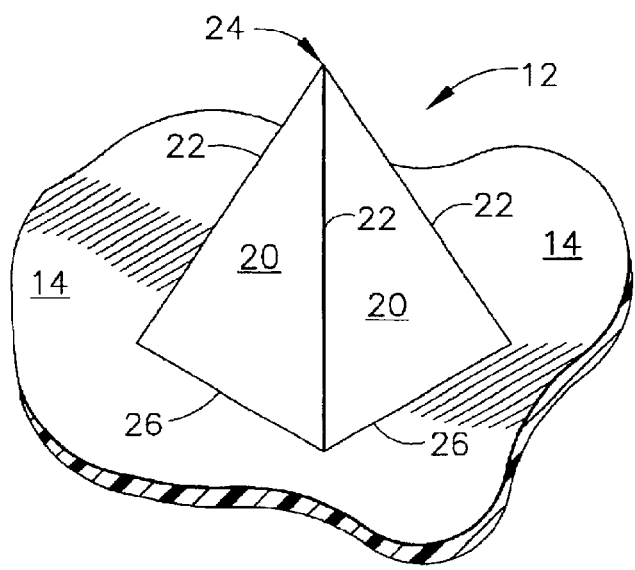
FIG. 2 is a perspective view of one of the pyramidal microelements of FIG. 1.

FIG. 2 illustrates in a magnified view one of the microelements 12, which has the appearance of a four-sided pyramid. Each side wall of the pyramid is designated at the reference numeral 20, and the seam or "corner" between sides is located at the reference numeral 22. The pyramid's peak is illustrated at 24, and the base line of each of the sides is located at 26, where it meets the substrate 14.

This array 10 of microelements is very useful in skin preparation by forming it into a patch that can be held by a human hand, and placed against a particular area of skin and then rubbed in a straight back and forth motion (or perhaps in a circular motion, if desired). When the patch or array 10 is rubbed against the skin, the microelements 12 will tend to remove skin cells that will accumulate in the planar spaces between the individual microelements 12. Since the skin cells that are removed do not become airborne, the microstructure array or patch 10 is a great improvement over the previously available mechanical scrubbers. Instead of knocking skin cells loose, the invention of FIG. 1 will trap the loose skin cells, which will then be disposed of along with the microstructure array 10.

In essence, the microstructure array 10 is very useful for an exfoliation of the skin, which in essence will pre-treat the skin for a later application of a conditioner substance, if desired. In addition to removing the skin cells, the array structure can also remove and collect foreign substances or even hair that are found on the surface of the skin while the microelements are rubbed along the skin surface. Once the area between the pyramidal microelements 12 becomes "full" of removed or "loose" skin cells and other substances, then this microelement array 10 essentially loses its functionality. The amount of material (including the loose skin cells) that is removed by use of the microelement array 10 is controlled by the height of the individual microelements 12 and the spacings therebetween. This allows fairly precise control over the number of layers of skin cells that are removed.

The array or patch 10 will correctly perform its functions of scraping and removing skin cells without regard to the direction of movement of the patch 10 with respect to the orientation of the individual microelements 12. In other words, these microelements 12 are omnidirectional in operation, and all directions are preferred, or even "predetermined." Other embodiments of the invention described below are not omnidirectional, and instead are unidirectional or bi-directional in nature with respect to the orientation of their individual microelements.

One very important aspect of the present invention utilizes the above rubbing/scraping feature, by which skin cells and other materials are first scraped loose, and then removed from the skin surface. The "precise control" noted above in connection with removal of the number of layers of skin cells is a "self-limiting" feature, in that the substrate-microelement combination (i.e., the microstructure patch 10 itself) will only remove a substantially predetermined quantity of these skin cells and materials before becoming "full," after which the patch 10 essentially will not remove any further skin cells/materials. The system is basically foolproof! Even if the user, either out of ignorance or exuberance, attempts to continuously re-use the patch, it will not further "scrape" the user's skin. After the patch 10 has accumulated the maximum amount of material that it can nominally hold, any additional skin cells removed by such further attempts to scrape the skin will be minuscule in quantity, and such further scraping attempts are essentially futile.

Similar microstructures are described below, although most of them exhibit different shapes for their microelements that protrude from the substrate. It will be understood that, regardless of the shape or size of the individual microelements, each of the microstructure patches described herein will have the capability for providing this fool-proof result. This is a significant improvement over previously-available devices that have been used for conditioning skin.

Another feature of the microstructure 10 is its capability for use in applying a conditioner or other type of compound that is in the form of a liquid or a cream. Just after the microstructure patch 10 has "cleansed" (exfoliated) an area of skin, the skin's surface will be smoother and mostly free of foreign substances. It is the perfect time to apply a fluidic compound, such as a conditioner, to the skin. The conditioner could enhance the health of the skin, or be in the form of make-up, for example. It also could be some type of topical drug or other active, if desired. The other microstructures described below will also lend themselves well for this type of topical application of a fluidic compound to skin.

A further feature of the microstructure 10 is its capability for a compound to be applied onto the substrate 14 and/or microelements 12 in advance of its placement against an area of skin. When the microstructure patch 10 is placed onto the skin, it will impart some of this compound onto the same area of the skin that is being cleansed, or exfoliate—this will essentially occur simultaneously. The other microstructures described below will also lend themselves well for this type of simultaneous delivery of a fluidic compound to the same area of skin that is being exfoliated. Of course, the embodiments described below which include through-holes in the substrate (e.g., see FIGS. 3 and 4) may not be the first choice for this methodology of composition delivery, but such devices certainly could be used in this manner, if desired. The compound that is pre-applied to the surface of the microstructure 10 could be placed either by the user, or at the time of manufacture of the microstructure 10.

Figure 3:
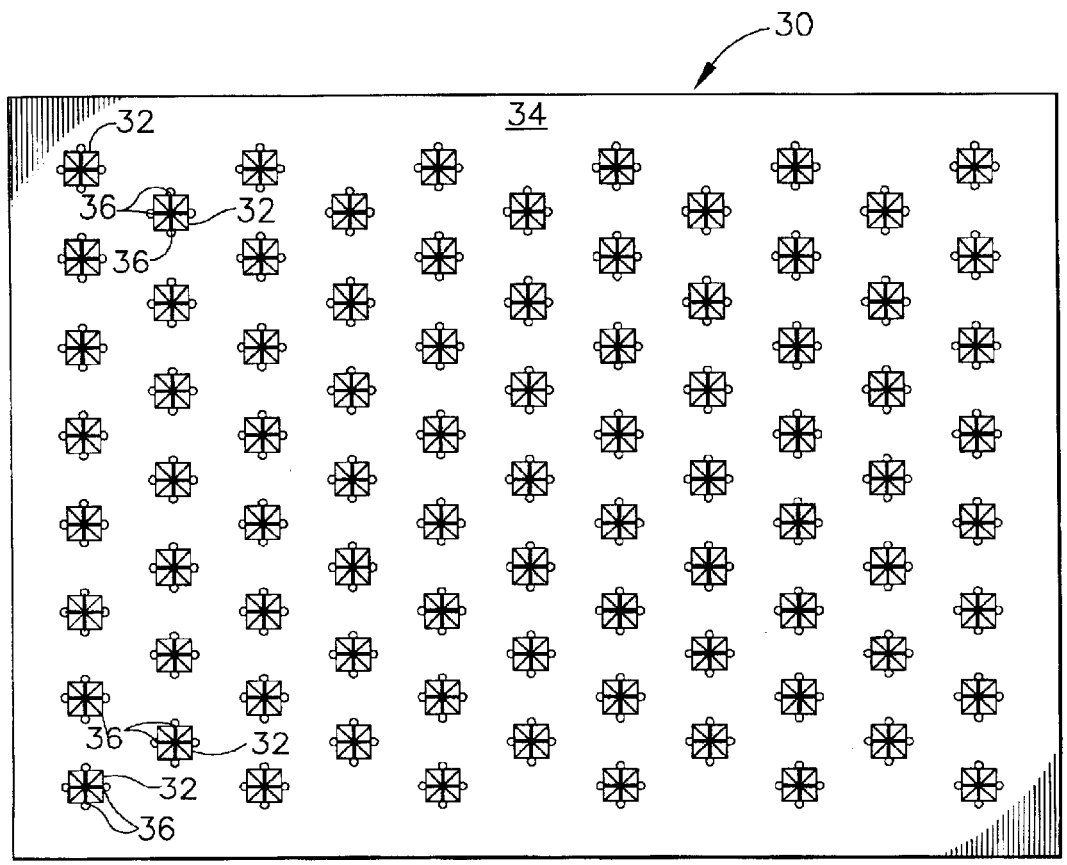
FIG. 3 is an array of pyramidal microelements as according to FIG. 1, with the addition of through-holes in the substrate, and channels along the sides of the microelements.

FIG. 3 illustrates a similar microelement array, generally designated by the reference numeral 30, in which through-holes and channels are added. The base or substrate 34 includes a plurality of through-holes 36 that are positioned proximal to the base of the individual pyramidal microelements 32. These through-holes 36 can either penetrate through the entire substrate 34, or can penetrate partially into the substrate and connect to passageways that may run in a direction perpendicular to the through-holes, and make common connections between many of the through-holes.

Figure 4:
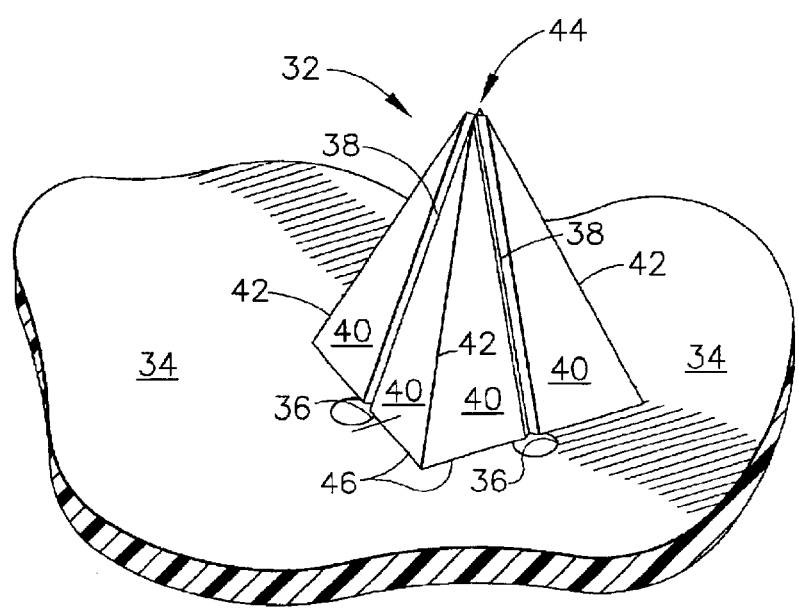
FIG. 4 is a perspective view of the pyramidal microelements of FIG. 3.

On FIG. 4, further details are visible, in which the side walls 40 of the pyramidal microelement 32 are seen to have grooved channels 38 which connect to the through-holes 36. The edges of the side walls 40 are at reference numeral 42, the individual base lines of the pyramid are at 46, and the peak of the pyramid is at 44.

On FIGS. 3 and 4, the array 30 of multiple pyramidal structures at 32 all have a through-hole adjacent to each side of the pyramid. Of course, there could be fewer through-holes 36 per pyramidal microelement 32, if desired. Alternatively, some of the pyramidal microelements 32 in the array could have no adjacent through-holes, if desired. Such microelements (or others in the array) could also forego the channels 38.

The structure of FIGS. 3 and 4 is useful to perform a simultaneous exfoliation and conditioning step. While the array or "patch" 30 is rubbed along the skin, the removed or loose skin cells will accumulate in the open spaces between the individual pyramidal microelements 32, which will prepare the skin for any type of conditioning that will then be placed upon that skin surface. Even after the "spacing areas" between the microelements 32 become essentially full of loose skin cells and oils or other substances found on the skin surface, at least one active or conditioner can nevertheless be delivered through the grooves or channels 38 by use of a capillary force. Moreover, the loose skin cells will not necessarily be tightly jammed along the surfaces of the pyramidal microelements 32, and therefore, should not become a significant obstacle to the delivery of the active or conditioner along the channels or grooves 38. Furthermore, the capillary force will work to the advantage of delivering a conditioner or active, especially in partially-blocked grooves or channels 38.

Similar to the patch 10, the array or patch 30 will correctly perform its functions of scraping and removing skin cells without regard to the direction of movement of the patch 30 with respect to the orientation of the individual microelements 32. In other words, these microelements 32 are omnidirectional in operation, and all directions are preferred, or even "predetermined."

Figure 5:
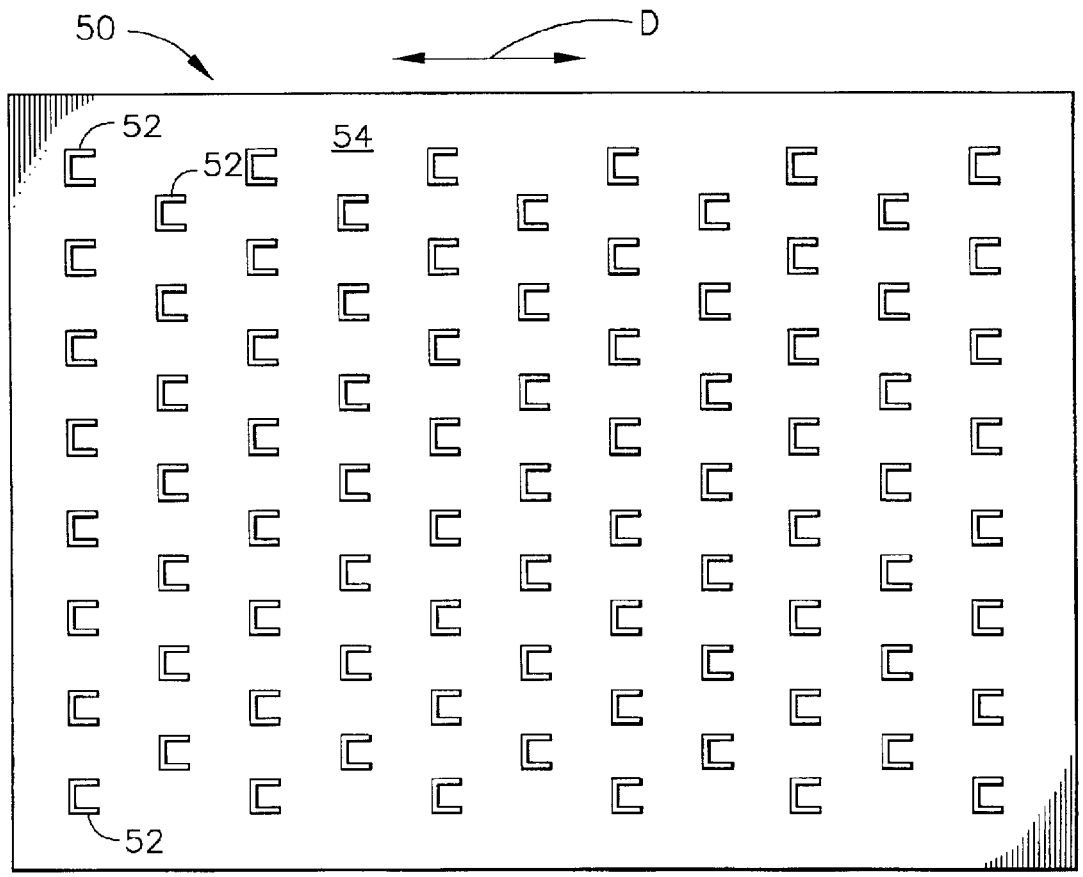
FIG. 5 is a plan view of an array of microelements that have an overall cubic rectangular shape, as constructed according to the principles of the present invention.

Another microelement shape is illustrated in FIG. 5, comprising an array 50 of "cubic rectangular" microelements at 52. These microelements 52 have a cup-like shape which has the appearance of a topless, hollow or open cube-like or box-like structure after one of the cube's (box's) side walls have been removed. This can be clearly seen in the perspective view of FIG. 6. (It will be understood that the "cube-like structure" 52 does not have identical length, width, and height outer dimensions, and thus is not really a geometric cube. In that respect, the term "box-like" or "box" is more descriptive.)

The individual columns of microelements 52 can be offset on the substrate 54, as seen in FIG. 5. As an alternative construction, each of the individual columns of these microelements 52 could be identical, thereby eliminating any offset, if desired. As a further alternative, there could be several columns with various offsets before the microelement pattern repeats, or the offsets could be substantially random so that there is no repetitive pattern.

To perform an exfoliation of skin, the microstructure or "patch" 50 is rubbed back and forth substantially along the direction designated by the letter "D" (which is a preferred, predetermined direction). In this manner, the open cup-like area will easily collect the loose skin cells and other foreign substances on the surface of the skin. The "open" area that will collect these cells is easily seen at 68 in FIG. 6.

Figure 6:
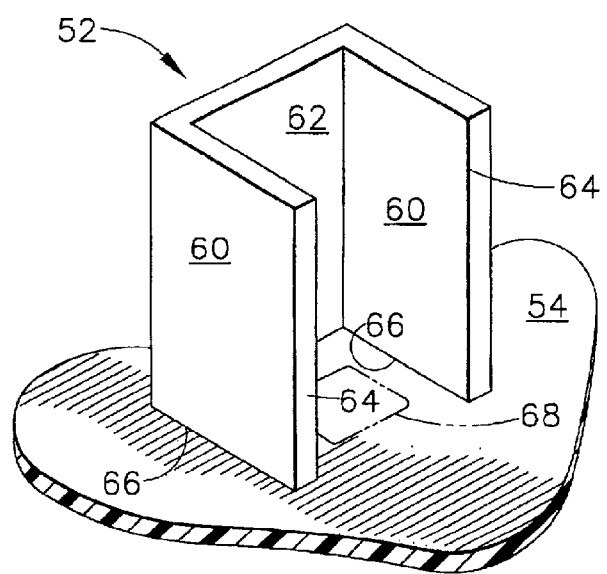
FIG. 6 is a perspective view of one of the cubic rectangular microelements of FIG. 5.

FIG. 6 shows further details of the individual microelement 52, which has a "back wall" 62, a pair of "side walls" 60, a "front edge" at 64 on each of the side walls 60, and a base line 66 along the bottom of the side walls 60.

As in the previously described embodiments, the amount of skin cells that can be collected by this structure 50 will depend upon the height of the individual microelements 52, as well as the spacings between such microelements on the substrate 54. The cup-like shape of the individual microelements 52 provides even better control over the quantity of material that is to be removed due to the rubbing action. Factors that impact the skin cell sizes to be removed (and the overall quantity of material to be removed) include the height of the walls 60 and 62, the open distance between edges 64 (i.e., the area 68), and the sharpness of the edges 64 themselves.

Figure 7:
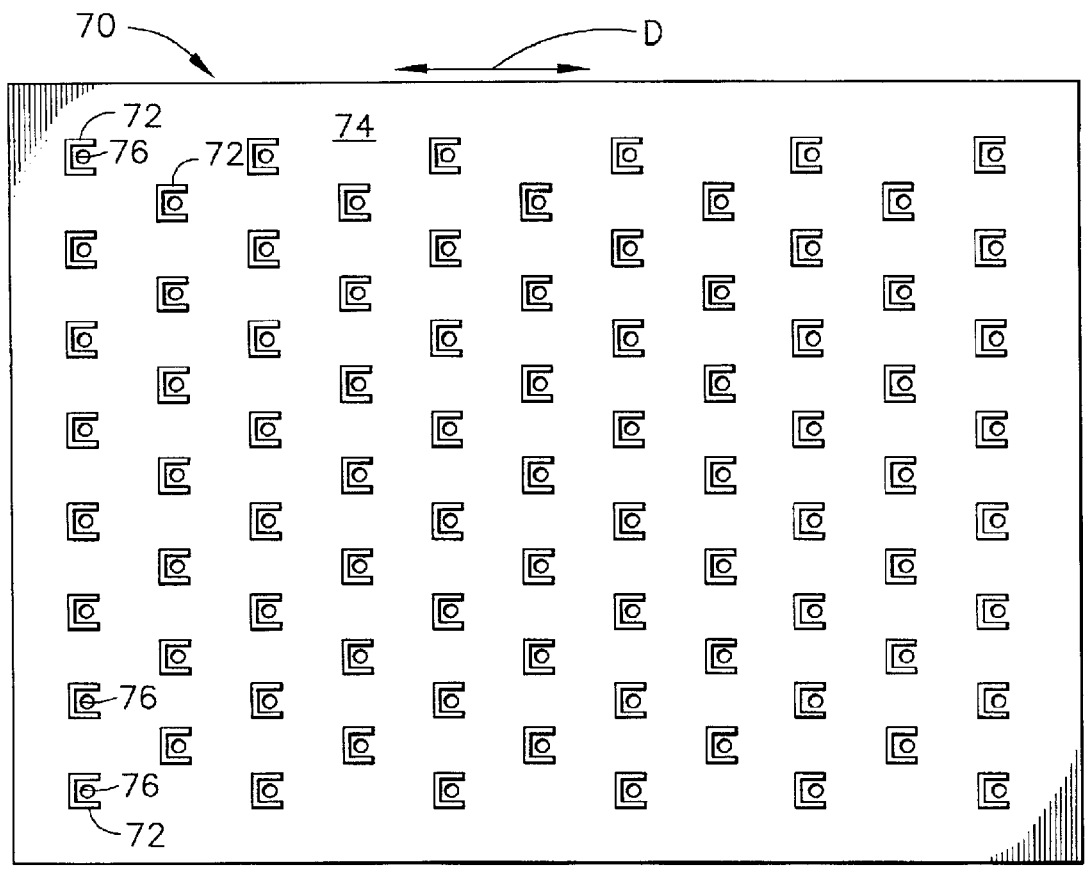
FIG. 7 is a plan view of an array of the cubic rectangular microelements of FIG. 5 with the addition of through-holes in the substrate.

FIG. 7 illustrates a similar array of microelements, designated by the reference numeral 70. Each individual microelement 72 has a similar appearance to the open box-like microelements 52 of FIGS. 5 and 6, however, a through-hole 76 has been added within the "cup-like" area of the microelement 72. These holes typically would run completely through the base or substrate 74, although they could instead extend only partially into the substrate to connect to some type of internal channels. In that manner, these holes could become (or connect to) passageways of any shape, diameter, or length.

Figure 8:
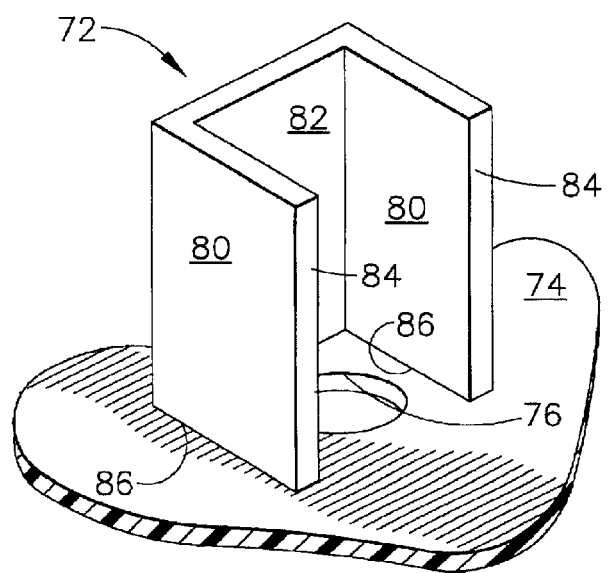
FIG. 8 is a perspective view of one of the cubic rectangular microelements of FIG. 7.

The microstructure array 70 could be formed into a "patch" that is applied to skin and rubbed in a back and forth manner substantially in the direction "D" indicated on FIG. 7 (which is a preferred, predetermined direction). FIG. 8 shows further details, in which there are two side walls 80, a back wall 82, two "front" edges 84, a base line 86 for each of the side walls 80, and the through-hole 76 that is proximal to the interior area of the microelement 72. In a similar manner to the previously described microstructure of FIGS. 3 and 4, the microstructure 70 disclosed on FIGS. 7 and 8 can be used to simultaneously exfoliate the skin surface while delivering some type of active that will condition the skin, or otherwise treat the skin. Such systems can both exfoliate and deliver in a single operation.

Figure 9:
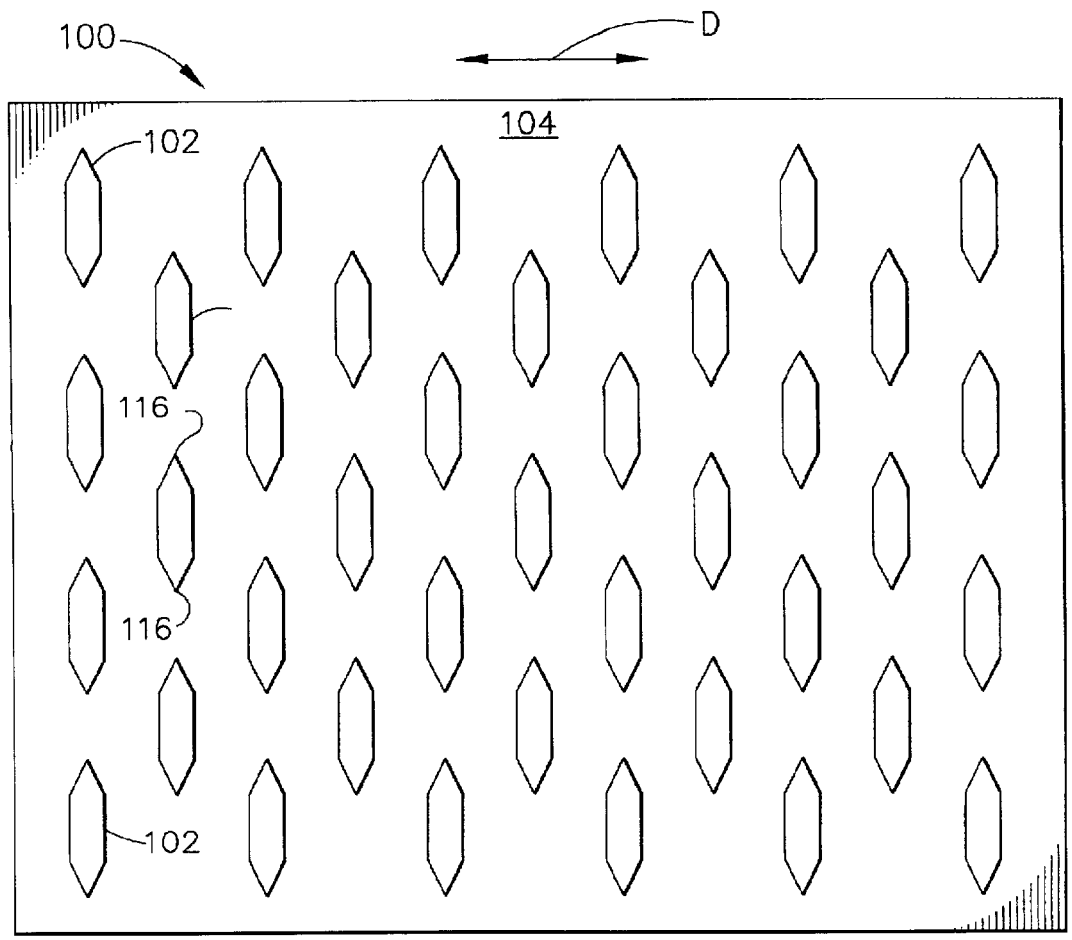
FIG. 9 is a plan view of an array of wedge-shaped microelements, as constructed according to the principles of the present invention.

FIG. 9 illustrates an array 100 of wedge-shaped microelements 102 mounted onto a base or substrate 104. As in some of the earlier-described embodiments, each column of microelements 102 can be offset from the adjacent column, as illustrated on FIG. 9. However, the columns could alternatively be made identical to one another, in which there would be no offset. A further alternative could arrange several columns with various offsets before the microelement pattern repeats, or the offsets could be substantially random so that there is no repetitive pattern.

Figure 10:
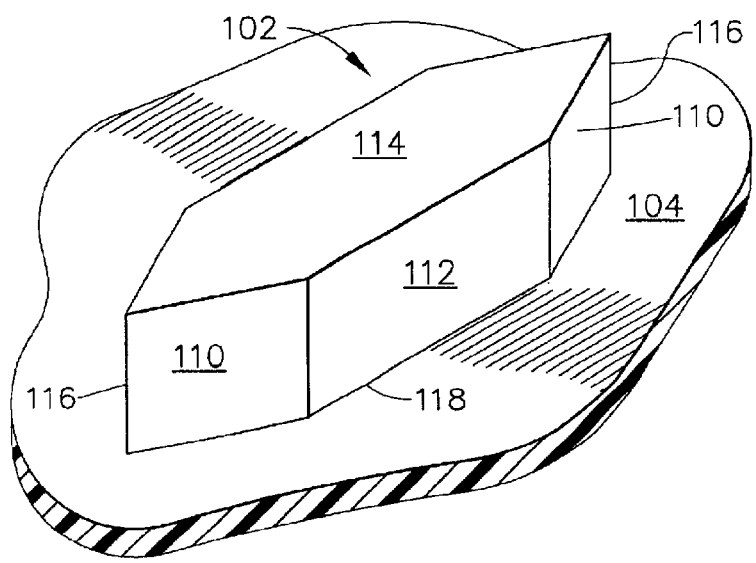
FIG. 10 is a perspective view of one of the wedge-shaped microelements of FIG. 9.

The wedge-shaped microelement 102 is illustrated in greater detail in the perspective view of FIG. 10. The top of the structure is at 114, and there are two elongated side walls 112 and a pair of converging side walls 110 that, at their line of convergence, form a cutting edge 116. There is also a base line 118 at the junction between the side wall 110 and the substrate 104.

The relatively sharp edge 116 is not purposefully used to "cut" skin in the exfoliation methodology described in this patent document. Instead, the overall wedge shape of the microelement 102 is provided as a more substantial structure than some of the other embodiments described herein. It also is probably easier to manufacture than the microelements described earlier, in FIGS. 1-8. In the microelements of the array 100 on FIG. 9, it is preferred to apply the array as a "patch" onto skin, and then rub it in a back and forth manner substantially along the line "D" (which is a preferred, predetermined direction). As can be seen from FIG. 9, the relatively sharp edges 116 will not be used to cut into the skin when the patch 100 is moved in this manner along the line "D." Rather than cutting the skin, the microelement patch or array 100 is designed to exfoliate the skin and accumulate skin cells and other foreign substances that have accumulated on the skin. The amount of removed skin cells and foreign substances that will be accumulated on the microelement array 100 depends upon the height of the individual microelements 102 and the spacings therebetween.

Figure 11:
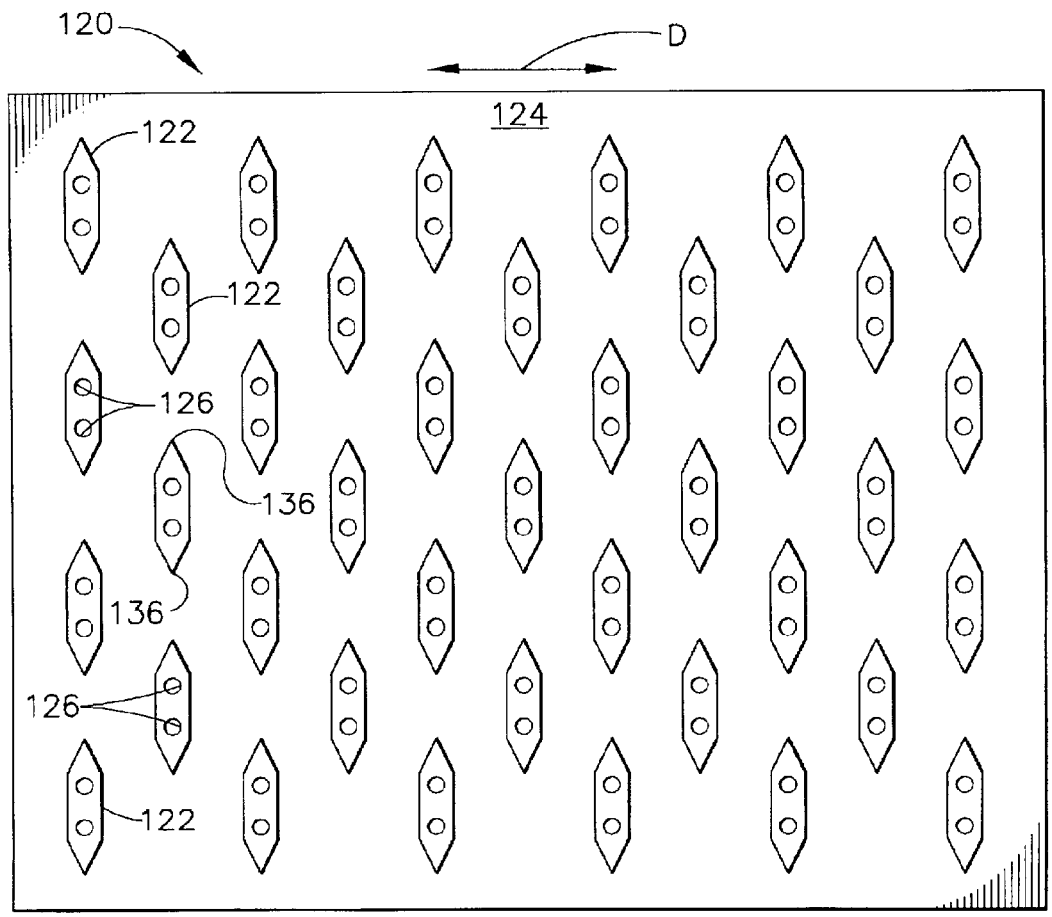
FIG. 11 is a plan view of an array of the wedge-shaped microelements of FIG. 9 with the addition of through-holes that penetrate through the microelement and through or into the substrate.

FIG. 11 shows a similar wedge-shaped microstructure array at 120, which has individual wedge-shaped microelements 122 that have two separate through-holes at 126. The microelements 122 are all mounted on a base or substrate 124. As viewed in FIG. 11, the columns of microelements 122 are somewhat different from one another, in that they are offset from one another in adjacent rows. This need not be the case, and alternatively the columns could be identical to one another to eliminate any offset, if desired. Again, alternatively there could be several columns with various offsets before the microelement pattern repeats, or the offsets could be substantially random so that there is no repetitive pattern.

Figure 12:
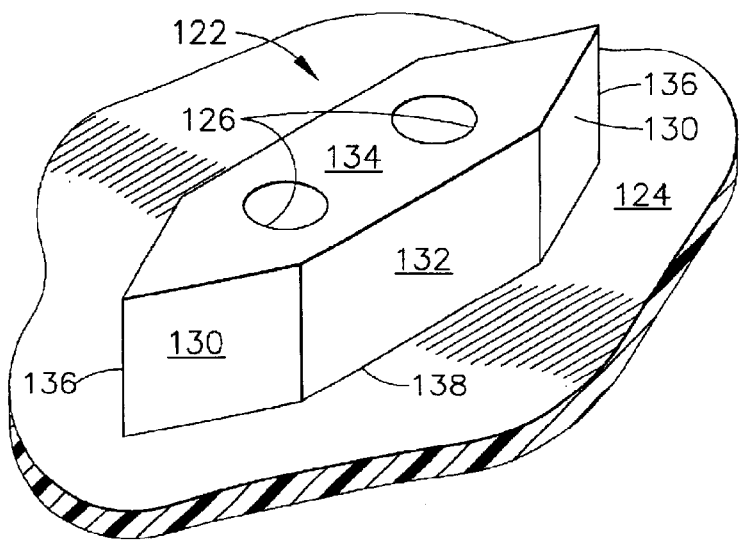
FIG. 12 is a perspective view of one of the wedge-shaped microelements having through-holes of FIG. 11.

FIG. 12 shows further details of the individual microelement 122, in which a top surface 134 and elongated side walls 132 are exhibited, along with converging side walls 130 that come to a sharp edge 136. A base line 138 is also illustrated as the junction between the microelement 122 and the substrate 124. The through-holes 126 are created to penetrate entirely through the microelement 122, and preferably will also penetrate entirely through the base 124, although the holes 126 can become passageways that do not entirely penetrate through the base or substrate, but instead connect to some type of perpendicular runs or passageways, if desired. Since there are two separate holes 126 per microelement 122, it is possible to simultaneously deliver two different actives (one per hole in a single microelement) in a single operation, if desired.

The microelements 122 are designed to perform both an exfoliation and delivery procedure in a single step. In this particular structure, it can almost be guaranteed that there will be a lack of build-up of dead skin and other foreign matter within the delivery holes or passageways 126. Even if some of this foreign matter or dead skin cells accumulates in these passageways 126, a capillary action may result and accomplish delivery of at least one active or drug through the passageways 126 onto the surface of the skin.

Figure 13:
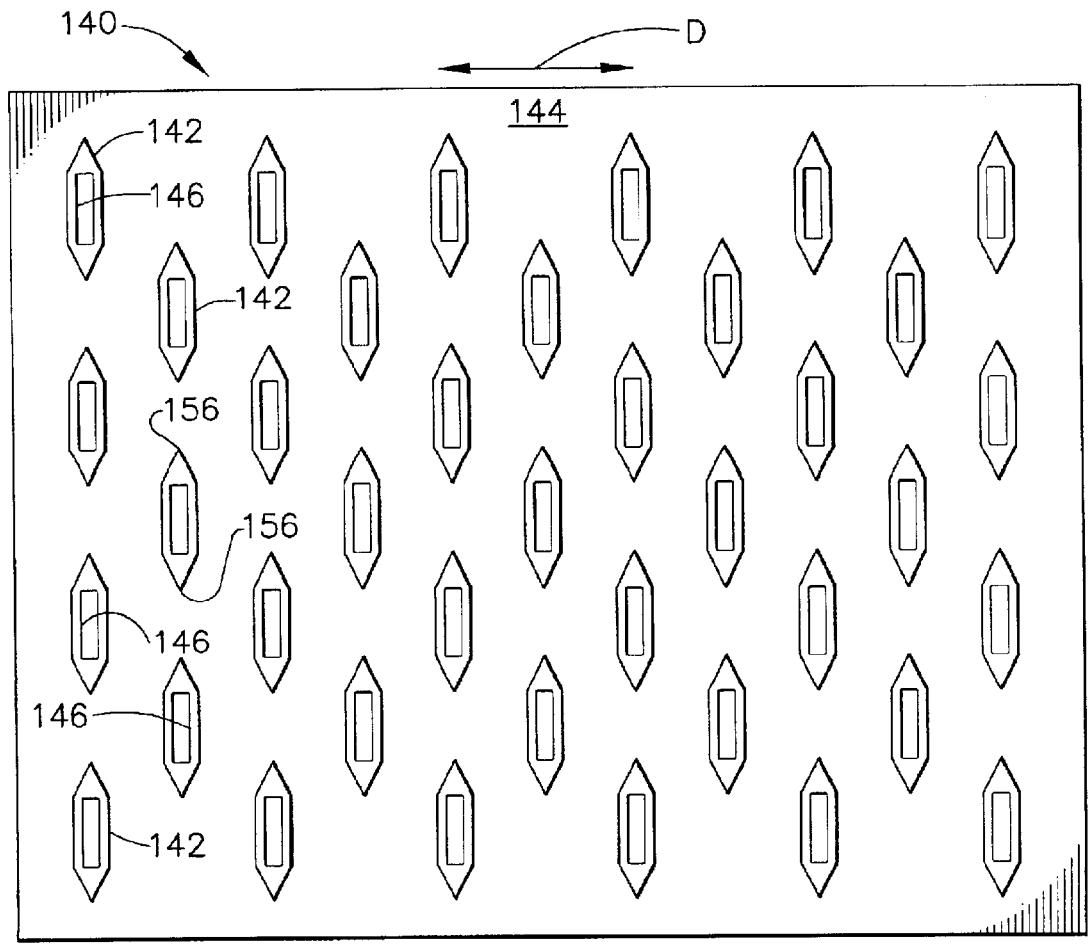
FIG. 13 is a plan view of an array of wedge-shaped microelements of FIG. 9, in which a through-slot is located in the microelements, which penetrates through or into the substrate.

FIG. 13 illustrates a microstructure array designated by the reference numeral 140 that contains a large number of individual wedge-shaped microelements 142 that are mounted to a base or substrate 144. These wedge-shaped microelements 142 contain a through-slot 146, through which at least one active or drug can be delivered to a skin surface after an exfoliation operation has taken place. In a similar manner to the structures of FIG. 11, the microelement array or patch 140 will preferably be placed on the skin surface and rubbed in a back and forth manner substantially along the direction "D" (which is a preferred, predetermined direction) to remove skin cells and other foreign substances from the skin surface. The amount of material removed from the skin surface will depend upon the height of the individual microelements 142 and the spacings therebetween.

Figure 14:
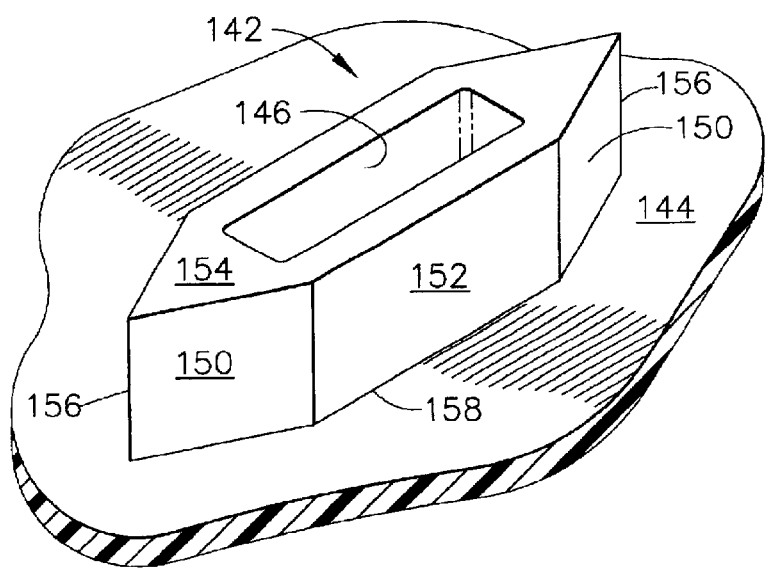
FIG. 14 is a perspective view of one of the wedge-shaped microelements having the through-slot of FIG. 13.

FIG. 14 shows greater details of an individual microelement 142, showing a top surface 154, side walls 152, converging side walls 150 that come to a relatively sharp edge 156, and a base line 158 where the microelement 142 adjoins the base or substrate 144.

The through-slot 146 can provide a larger cross-sectional area for delivery of at least one active or drug to the skin surface, as compared to the microelement 122 of FIG. 12. Of course, the actual dimensions of the microelement 142 could be either larger or smaller than similar microelements 122 illustrated on FIG. 12. Both sets of microelements 122 and 142 are relatively simple to construct, although the ones with the through-slot 146 may be somewhat easier to construct as compared to constructing multiple smaller through-holes 126.

The patch or array 140 can be used for a combinational step of exfoliation and delivery of at least one active, in a similar fashion to that described in some of the earlier embodiments. Other similar shapes of wedge-shaped structures could easily be constructed without departing from the principles of the present invention.

Figure 15:
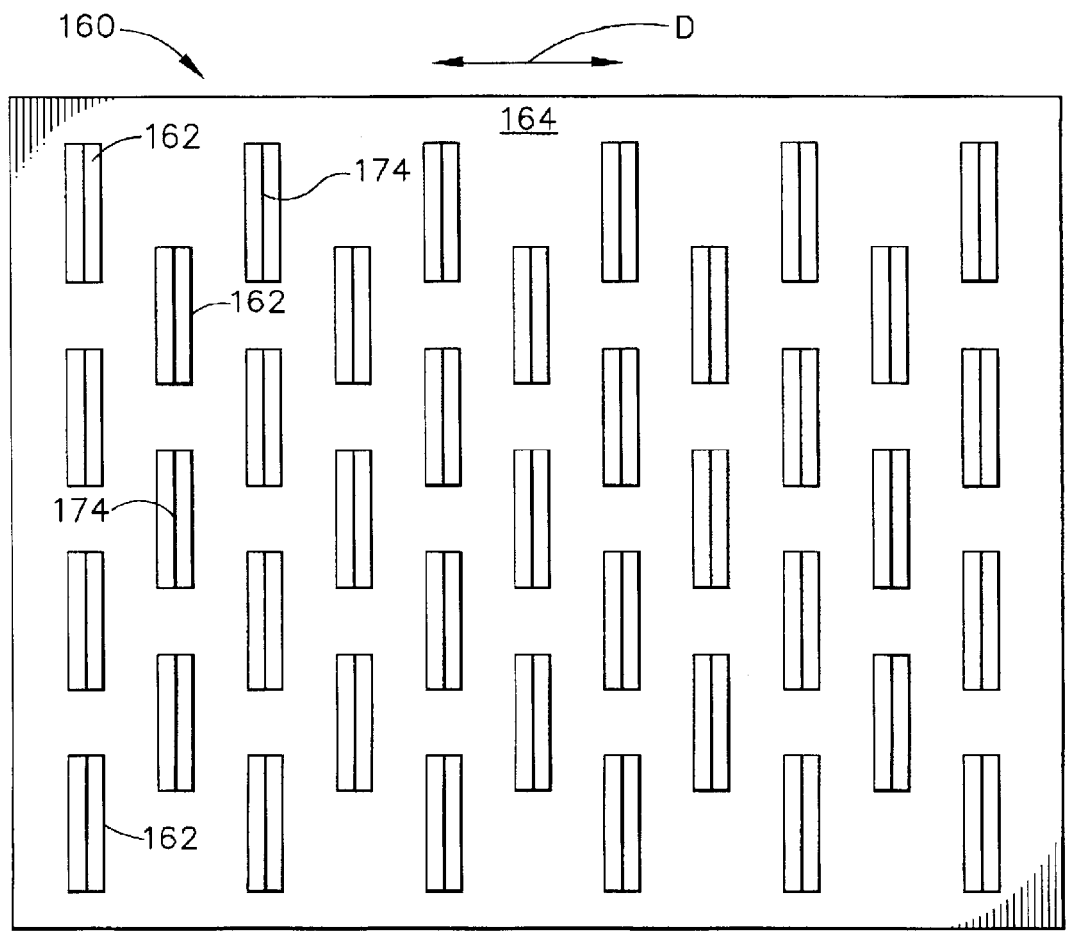
FIG. 15 is a plan view of an array of microelements having an elongated triangular shape, as constructed according to the principles of the present invention.
Figure 16:
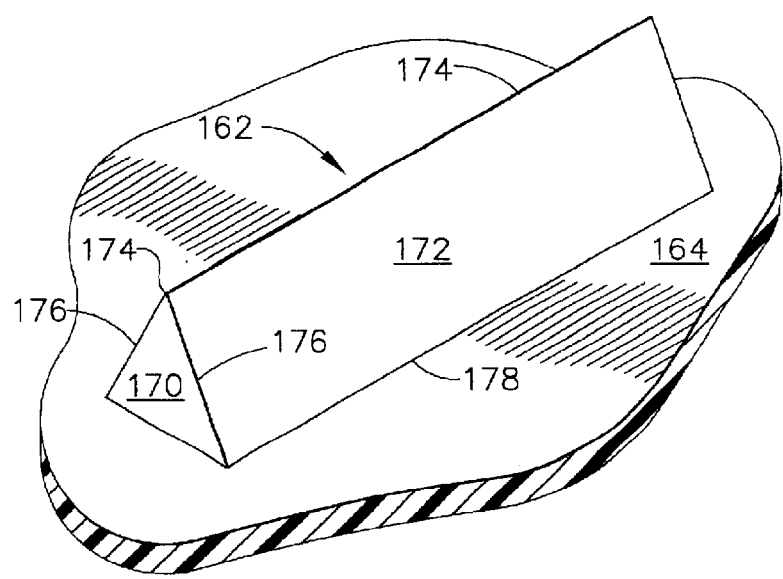
FIG. 16 is a perspective view of one of the elongated triangular microelements of FIG. 15.

FIG. 15 discloses an array or patch 160 of triangular-shaped wedge microelements 162, mounted on a base or substrate 164. As seen in FIG. 16, each of the microelements 162 consists of an elongated triangular shape, having a pair of triangular side walls 170, a pair of sloped elongated side walls 172, a top edge 174, and a pair of base lines 178. The junction between the triangular end walls 170 and the rectangular but sloped side walls 172 is designated at the reference numeral 176. The peak of the triangle is illustrated at 174, which is only one point along the top edge 174 of the microelement 162.

These triangular-shaped wedges can be useful in an exfoliation procedure, and preferably will be placed on skin in the form of a patch and then rubbed back and forth over the skin substantially in the direction "D" (which is a preferred, predetermined direction). The amount of loose skin cells that are removed (and the amount of any additional foreign substances removed) will depend upon the overall height of each of the microelements 162 and the spacings therebetween. The individual columns of microelements can be offset from one another in adjacent columns, as seen in FIG. 15. Alternatively, the columns could be identical to one another, without any offset. Another alternative could arrange several columns with various offsets before the microelement pattern repeats, or the offsets could be substantially random so that there is no repetitive pattern.

Figure 17:
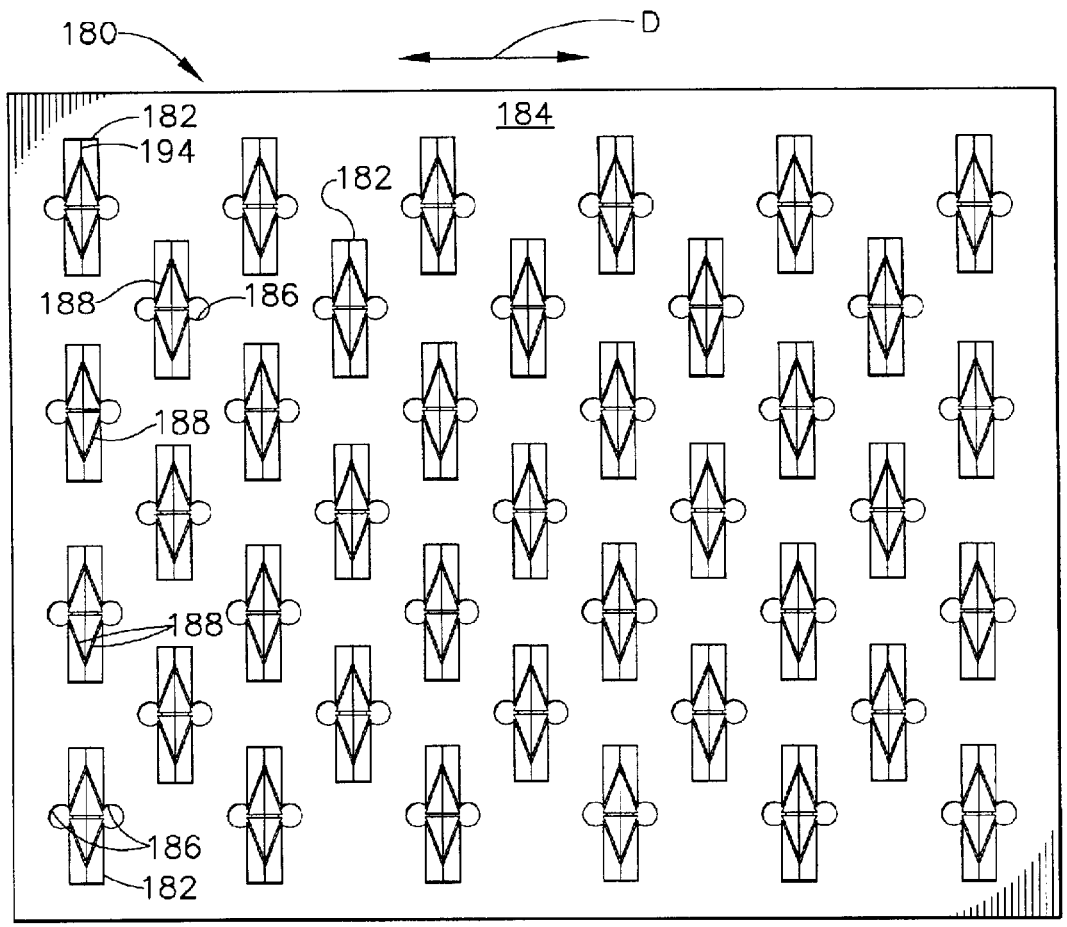
FIG. 17 is a plan view of an array of the elongated triangular microelements of FIG. 15 with the addition of through-holes in the substrate, and elongated channels along the surfaces of the triangular microelements.

FIG. 17 discloses a similar microelement array 180, which has triangular-shaped wedges as individual microelements 182 that are placed or are formed upon a base or substrate 184. In the "patch" 180, there are multiple through-holes 186 and channels 188 for placing at least one active on the skin.

Figure 18:
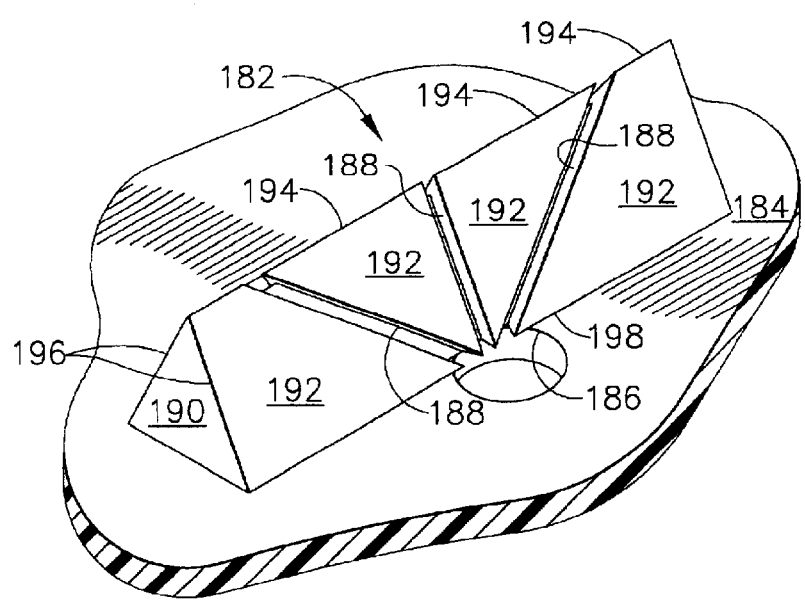
FIG. 18 is a perspective view of one of the elongated triangular microelements of FIG. 17.

FIG. 18 shows the channels 188 and holes 186 in a magnified view, in which the holes 186 would typically be designed to penetrate entirely though the substrate 184; however, such holes 186 could only partially penetrate the base if they connect to some other type of passgeway within the base structure itself.

The triangular shape of the microelement 182 is seen on FIG. 18 along the side wall 190, which connects to sloped, rectangular side walls 192 along edges 196. A top edge 194 exists between the two triangular side walls 190, and a base line 198 marks the line between the microelement 182 and the substrate 184.

On FIG. 18, there are three separate channels 188 in the surface of the elongated side wall 192. Of course, fewer channels could be utilized, if desired, or even more numerous channels could be used. These channels 188 lend themselves well for capillary action to allow at least one active to flow through the holes 186 and along the channels 188 onto a skin surface, even after the areas between the microelements 182 become substantially full of dead skin cells and other foreign substances.

The triangular wedge structures of both FIGS. 16 and 18 are designed to essentially scrape away dead skin cells without penetrating the skin itself. This is accomplished by moving the microelement patches 160 or 180 in a back and forth manner substantially in the direction "D" as shown on FIGS. 15 and 17. Of course if the microelement patches were to be moved in a different direction, particularly one that was perpendicular to the line "D" (which is a preferred, predetermined direction), then it is quite likely that the skin would be cut and penetrated. This has much usefulness, however, that concept is not part of the present invention. Instead, that type of methodology is disclosed in a companion patent application, Ser. No. 09/952,391 that is also assigned to The Procter & Gamble Company, and having the title "Microelements for Delivering a Composition Cutaneously to Skin."

Figure 19:
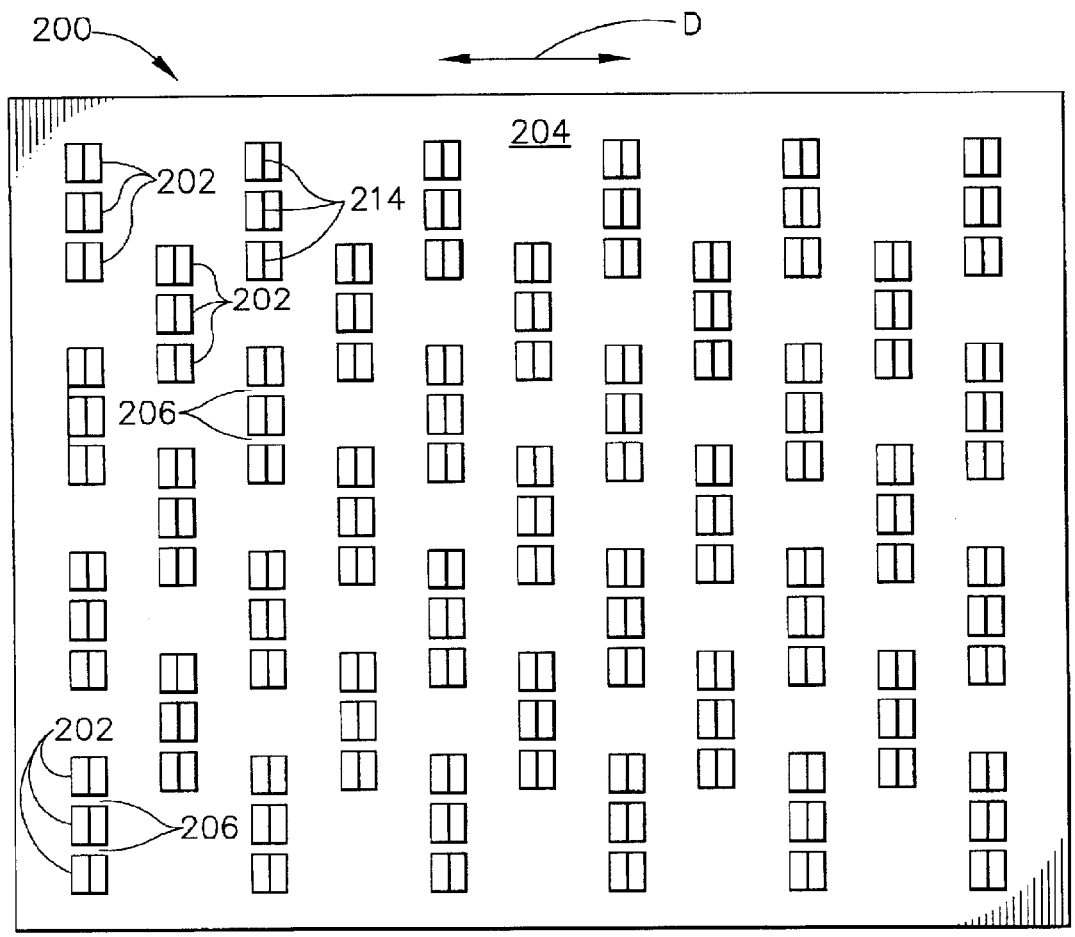
FIG. 19 is a plan view of an array of triangular-shaped wedge microelements that are grouped in closely-spaced arrangements, as constructed according to the principles of the present invention.
Figure 20:
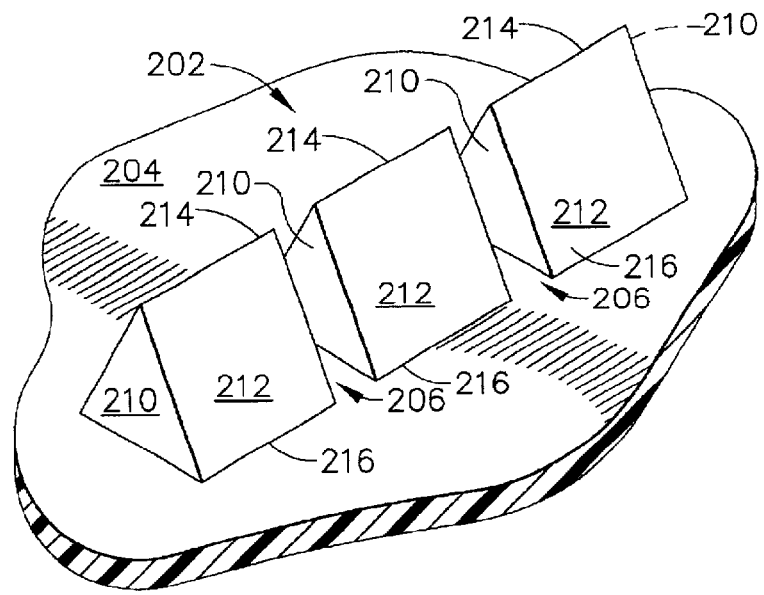
FIG. 20 is a perspective view of one of the closely-spaced triangular wedge microelements of FIG. 19.

Another refinement of the triangular-shaped wedge is illustrated on FIGS. 19 and 20. On FIG. 19, a microstructure array or patch 200 is illustrated as containing multiple wedge-shaped microelements 202 that are placed upon, or are formed thereon, a base or substrate 204. As seen in FIG. 20, each of the microelements 202 is comprised of three separate triangular-shaped wedges, each having a space therebetween at 206.

On FIG. 20, it can be seen that the three sections of the triangular-shaped wedge 202 includes a triangular-shaped side wall 210, a pair of rectangular, sloped side walls 212, a top edge 214, and a base line at 216 where the microelement 202 joins the substrate 204. Each of the three wedge shapes is separated by a space 206, in which a center triangular wedge shape is surrounded on both sides by a second, outer similar wedge shape, and spaced apart from each of these outer wedge shapes by the spacing area 206.

The "new" spaces 206 provide more trapping area between the closely-spaced wedges of the microelement 202. Therefore, a further amount of material should accumulate within these spaces, thereby trapping more dead skin cells and other foreign substances for a given microelement array or patch 200. As in the case of these embodiments described above, the amount of material that will be removed and then accumulated from the skin surface will depend upon the height of the microelements 202 and the spacings therebetween. In this new structure of FIGS. 19 and 20 this will also depend upon the spacings 206 between the individual triangular wedges of the individual microelement 202.

The preferred use of the array or patch 200 is to apply the patch directly to the skin, and then rub the patch in a back and forth manner along the skin surface substantially in the direction "D" as seen on FIG. 19 (which is a preferred, predetermined direction). This particular design exfoliates quite well, but is not designed to also apply an active at the same time. Of course, through-holes and channels could be added to this structure, if desired, although that type of structure would probably be easier to construct when using the shape disclosed in FIG. 18 for the microelement 182.

Figure 21:
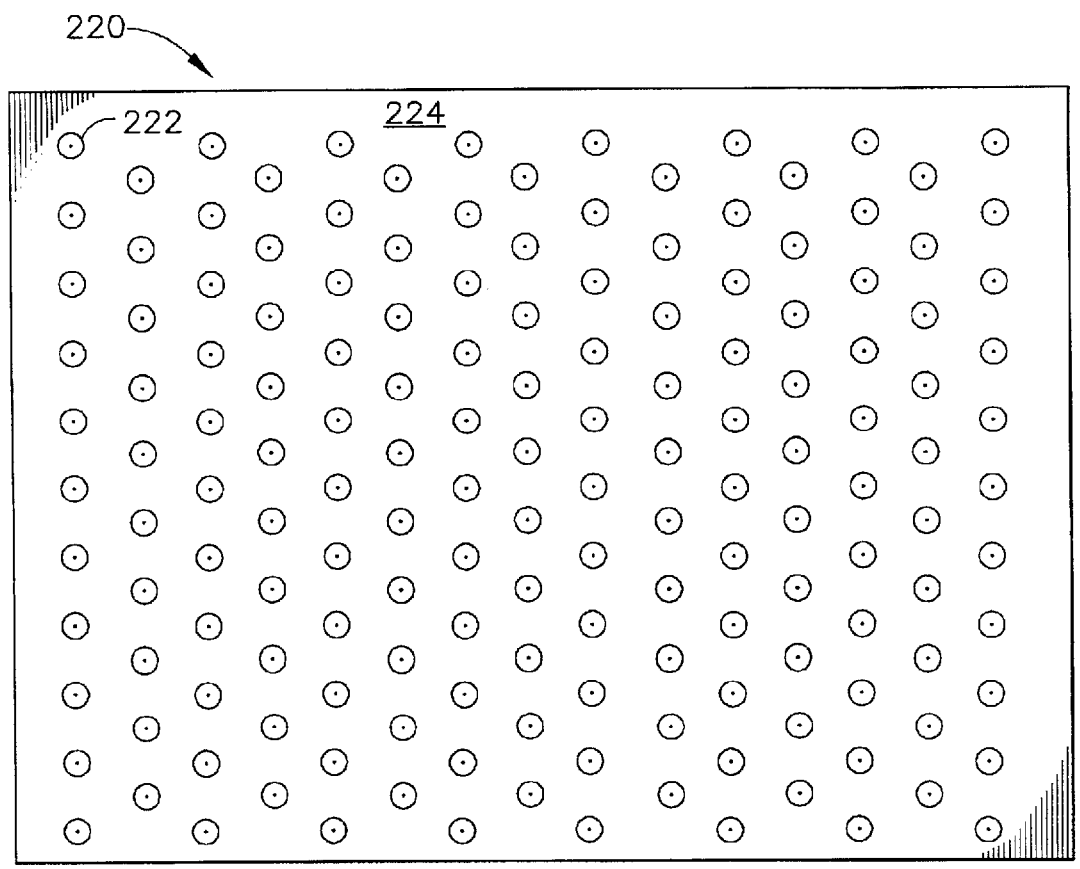
FIG. 21 is a plan view of an array of conical-shaped microelements, as constructed according to the principles of the present invention.
Figure 22:
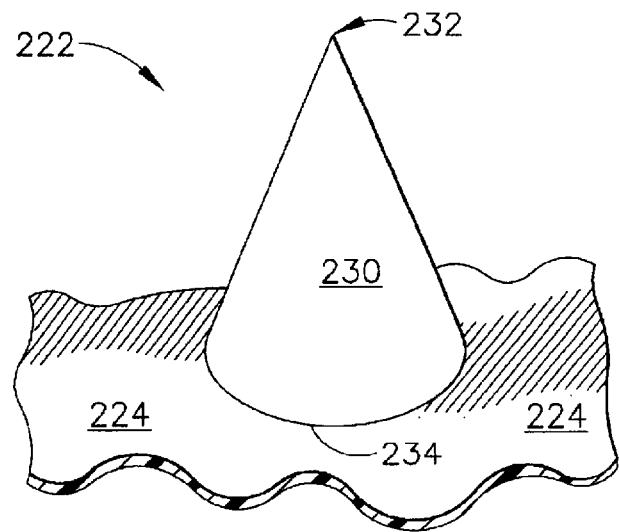
FIG. 22 is a perspective view of one of the conical microelements of FIG. 21.

FIG. 21 illustrates a microstructure array 220 that has multiple cone-shaped microelements 222 that are placed upon or constructed on a base or substrate 224. The individual microelements 222 are illustrated in greater detail in FIG. 22, in which each conical microelement 222 has a curved side wall 230, a peak 232, and a circular base "line" at 234. If desired, the conical shape of the microelement 222 could be somewhat truncated so that it does not come to a perfect point at 232. One advantage of having the curved side wall 230 is that it will more easily de-mold, thus simplifying fabrication.

The individual columns of the conical microelements 222 can be offset from one another for such adjacent columns if desired, as viewed in FIG. 21. Alternatively, each of the columns of microelements could be identical to one another, with no offset. Yet another alternative could arrange several columns with various offsets before the microelement pattern repeats, or the offsets could be substantially random so that there is no repetitive pattern.

The conical microelements 222 on the array or patch 220 can be used for exfoliation in a manner as described above for other shapes of microelements. In this particular structure, the direction of motion of the array or patch 220 is not important with respect to removing the skin cells or other foreign substances from the skin surface. From that standpoint, the microstructure patch 220 is similar to the patches 10 and 30 disclosed in FIGS. 1 and 3. As before, the amount of dead skin cells and other substances that are accumulated depends upon the height of the individual microelements 222 as well as the spacings therebetween.

Similar to the patch 10, the array or patch 220 will correctly perform its functions of scraping and removing skin cells without regard to the direction of movement of the patch 220 with respect to the orientation of the individual microelements 222. In other words, these microelements 222 are omnidirectional in operation, and all directions are preferred, or even "predetermined."

Figure 23:
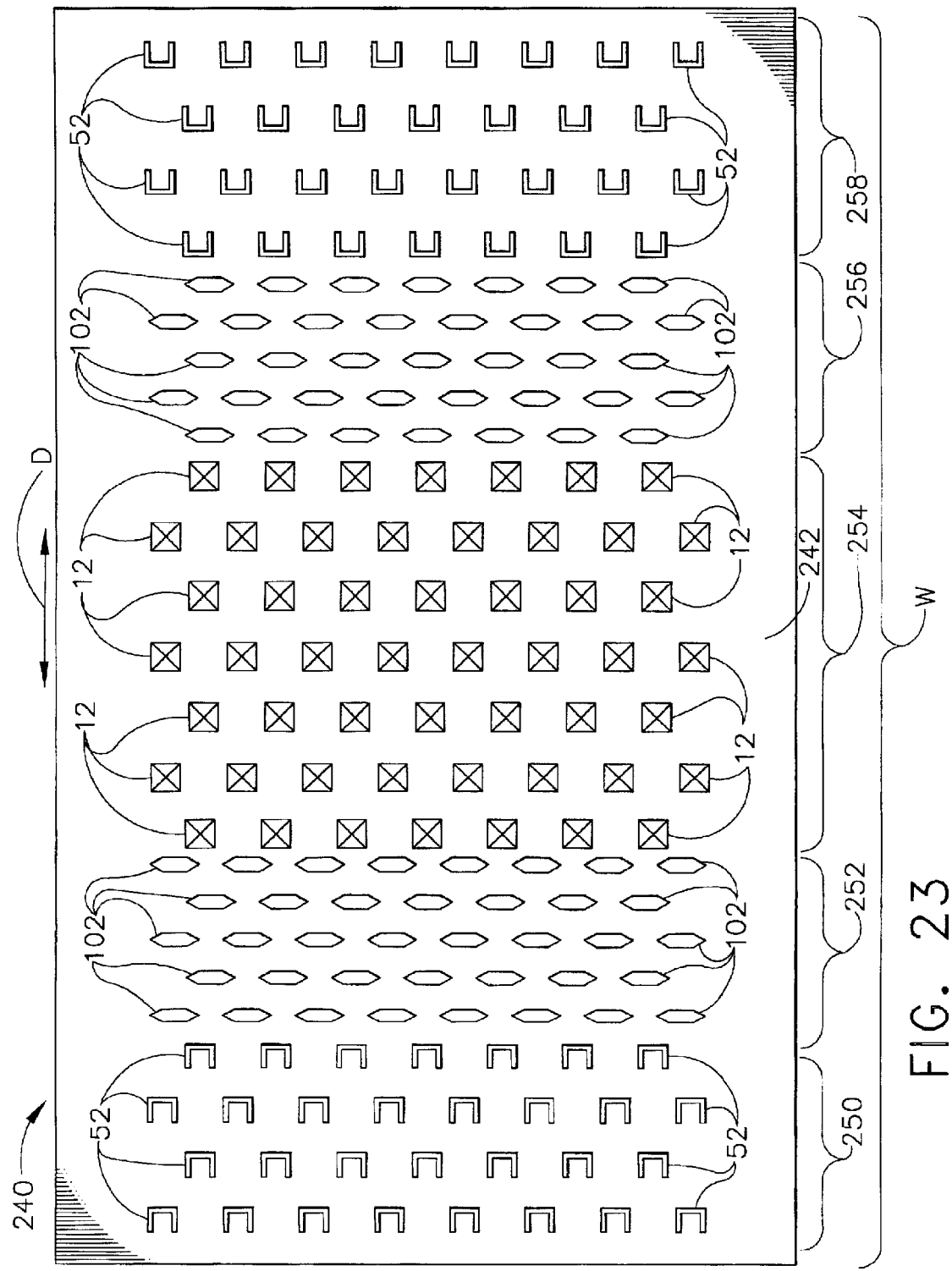
FIG. 23 is a plan view of a microelement array in which more than one microelement shape is constructed on the single substrate, as constructed according to the principles of the present invention.

FIG. 23 illustrates a microstructure array generally designated by the reference numeral 240 that contains more than one microelement shape upon its substrate 242. The different shapes are grouped in sub-arrays, which are designated by the reference numerals 250, 252, 254, 256, and 258. These multiple shapes on a single base or substrate could all be the same height, or if desired, could be of different heights. Furthermore, there could be through-holes or other types of passageways for delivering an active to a skin surface, or alternatively they could have no such passageways in the surface of the substrate 242 and the patch 240 could be used merely for exfoliation. On FIG. 23, the overall width of the array or patch 240 is designated by the dimension "W", which could be of any size necessary for a particular application.

On FIG. 23, the left-hand array 250 consists of multiple cup-shaped microelements 52, which were earlier described in reference to FIGS. 5 and 6. As seen in FIG. 23, these "open-box" or "cup-like" microelements 52 are facing to the left, which means that they would tend to accumulate skin cells when the array or patch 240 is moved toward the left along the arrow "D" (which is a preferred, predetermined direction). The width of this array 250 is about ⅙ W in the illustrated embodiment of FIG. 23; however, the width or array overall shape (i.e., it could be non-rectangular) could be easily varied, as desired.

A similar array of cup-like microelements 52 is arranged along the right-hand side (as seen in FIG. 23) in the array 258. These open-box microelements 52 would tend to accumulate skin cells when the microelement array or patch 240 is moved toward the right along the arrow "D" (which is still a preferred, predetermined direction). The width of this array 258 is also about ⅙ W in the illustrated embodiment of FIG. 23, but this too could be easily varied.

The microelements in the arrays 252 and 256 are illustrated as being the wedge-shaped elements 102 that were described above in reference to FIGS. 10 and 11. The middle array 254 is composed of the pyramidal microelements 12 that were described above in reference to FIGS. 1 and 2. The width of the arrays 252 and 256 are each about ⅙ W in the illustrated embodiment of FIG. 23; however, the width or array overall shape (i.e., it could be non-rectangular) could be easily varied for either of these arrays, as desired. Finally, the width of the middle array 254 is about ⅓ W in the illustrated embodiment of FIG. 23; however, as noted above, the width or array overall shape (i.e., it could be non-rectangular) could be easily varied, as desired.

If all of the microelements constructed on the array or patch 240 in FIG. 23 are of precisely the same height, this multiple microelement-shaped patch would nevertheless provide different treatments to the skin surface. For example, the pyramidal-shaped microelements 12 would provide a "fine" treatment and remove the smaller skin cells, while the wedge-shaped microelements 102 of the arrays 252 and 256 would provide a "medium" treatment and thereby remove somewhat larger skin cells. At the same time, the "end" arrays 250 and 258 that are composed of the cup-shaped (or open box) microelements 52 would provide a "coarse" treatment of the skin, and tend to remove the larger skin cells. In this manner, each individual area of the multiple-shaped array or patch 240 would tend to remove different sized skin-cells, thereby accomplishing a removal of at least most of all of the skin cells up to a certain depth into the stratum corneum. Of course, the types and sizes of skin cells that are removed could also be controlled by changing the height of some of the microelements of different shapes, if desired. As noted above, however, even if all of the microelements were of the same precise height, each of these array areas would tend to accumulate different sized skin cells.

It will be understood that a microelement patch could be composed of any one shape of microelements, or could be comprised of several different shapes on a single substrate or patch structure, without departing from the principles of the present invention. Moreover, it will be understood that the microelements disclosed herein could be of all the same height, or of different heights on the same substrate or patch, without departing from the principles of the present invention. Finally, it will be understood that minor modifications to the shapes disclosed in the drawings are contemplated by the inventors, and would still fall within the principles of the present invention.

It will also be understood that the microelement arrays or patches that contain through-holes or through-slots need not have such through-holes or through-slots for each and every one of the individual microelements that make up the array. In other words, the passageways that flow through the microelements (or adjacent thereto) could be constructed on only one-half of the microelements, if desired, while still achieving most of the results that would otherwise be achieved if such through-holes or through-slots were found at each of the microelements. Certainly, the holes or slots could be varied in size or diameter to either reduce or increase the amount of fluidic material that flows therethrough. All of these variations are contemplated by the inventors, and would fall within the principles of the present invention.

Figure 24:
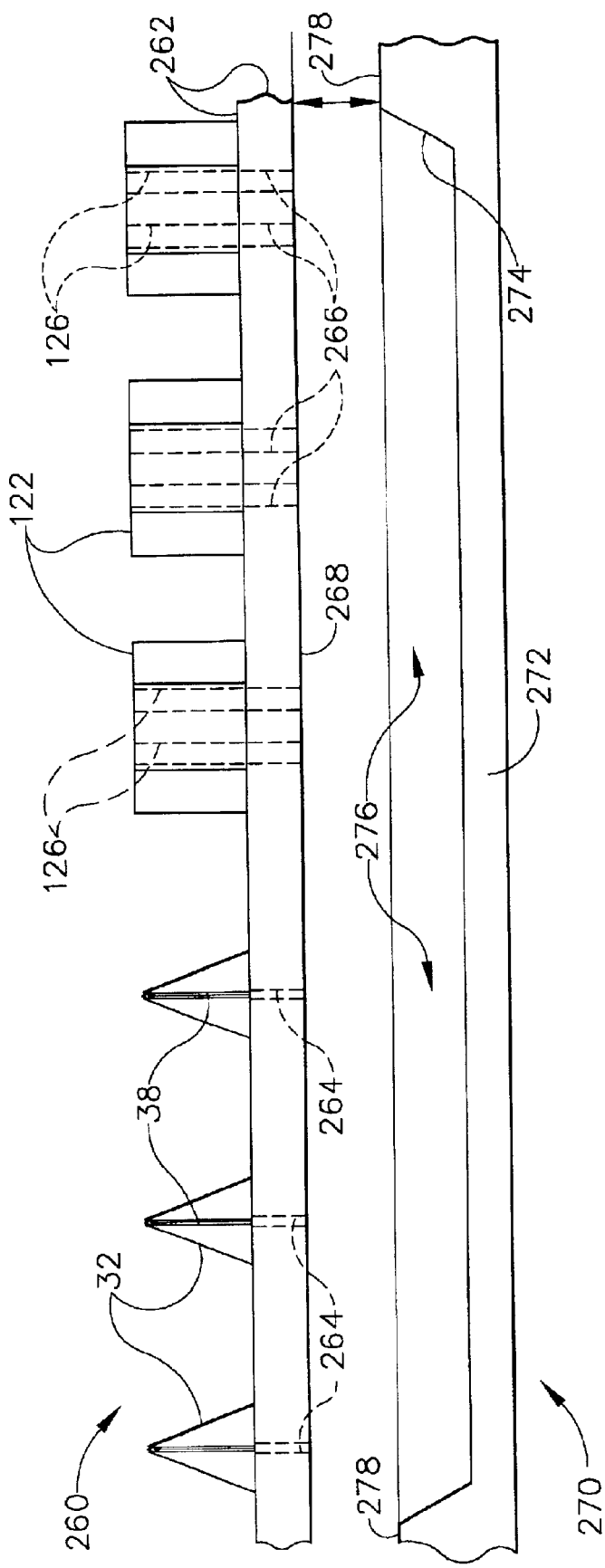
FIG. 24 is an elevational view in partial cross-section of an array of microelements similar to those found in FIG. 23, with the addition of through-holes or passageways to a reservoir structure below the main substrate.

FIG. 24 is a side elevational view in partial cross-section of a microstructure that contains an array of different shaped microelements and a corresponding substrate, designated at the reference numeral 260, as well as an underlying reservoir structure designated by the reference numeral 270. On FIG. 24, the array of microelements 260 is illustrated as having a set of pyramidal microelements 32 having grooves or channels 38 along the sides of the pyramid shapes, and a set of wedge-shaped microelements 122 having through-holes 126. The base or substrate is designated at the reference numeral 262.

On FIG. 24, the through-holes actually travel all the way through both the microelements and the substrate 262 to form passageways, and these passageways are depicted in two groups. The first group is a combination of the grooves or channels 38 in the pyramidal microelements 32 that are connected to the through-holes 264, to form a common set of passageways that extend from the bottom surface of the base or substrate 262 through the top surface of this substrate 262 and are in communication with the channels or grooves 38. The second set of passageways comprises a set of through-holes 266 that are in communication with the microelement through-holes 126 of the wedge-shaped microelements 122. These through-holes 126 and 266 must be in registration with one another to form complete passageways from the top of the microelement 122 to the bottom of the substrate of 262. Naturally, there could be some horizontal runs that connect similar passageways, if desired.

The bottom portion 270 depicted in FIG. 24 includes a reservoir structure that has a bottom wall at 272 and a reservoir area or volume at 276 that is bounded by the side walls of the reservoir at 274. Multiple such compartments or chambers can be constructed to house multiple actives. The upper portion of this reservoir structure 270 would typically be planar, as depicted at the reference numeral 278, and would make contact against the bottom surface at 268 of the microstructure/substrate apparatus at 260. It is important that the reservoir 276 be in communication hydraulically or pneumatically with the passageways 264 and 266, thereby allowing a fluidic drug or other active to reside within the reservoir confines at 276 until used, and then for the fluidic drug or active to be directed through the passageways 264 and 266 to the upper surface of the microelements 32 and 122.

Figure 25:
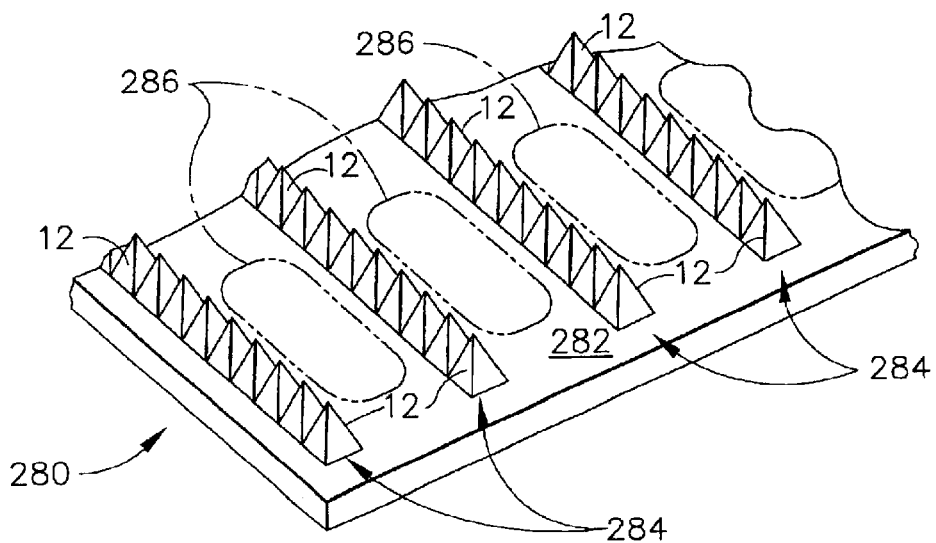
FIG. 25 is a perspective view of multiple arrays of pyramidal-shaped microelements, as constructed according to the principles of the present invention.

FIG. 25 illustrates a variation of the pyramidal microelements on a patch or array, generally designated by the reference numeral 280. Several columns of the pyramidal microelements are illustrated, in which the columns are at 284, and are composed of individual pyramidal microelements 12. These columns 284 of microelements are all built upon a planar substrate 282 of the array or patch 280. As can be seen in FIG. 25, there is no substantial space between individual microelements 12 within an individual column 284.

There is, however, a substantial space between adjacent columns 284, and these spacings are designated by the reference numeral 286 along the planar surface of the substrate 282. It is the spacings 286 that will accumulate skin cells and other foreign substances as these pyramidal microelements are used to exfoliate skin. In a preferred embodiment for use of the microelement array 280, the array/patch 280 will be placed upon skin and moved in a back and forth manner substantially along any line. Similar to the patch 10, the array or patch 280 will correctly perform its functions of scraping and removing skin cells without regard to the direction of movement of the patch 280 with respect to the orientation of the individual microelements 12. In other words, these microelements 12 are omnidirectional in operation, and all directions are preferred, or even "predetermined."

Figure 26:
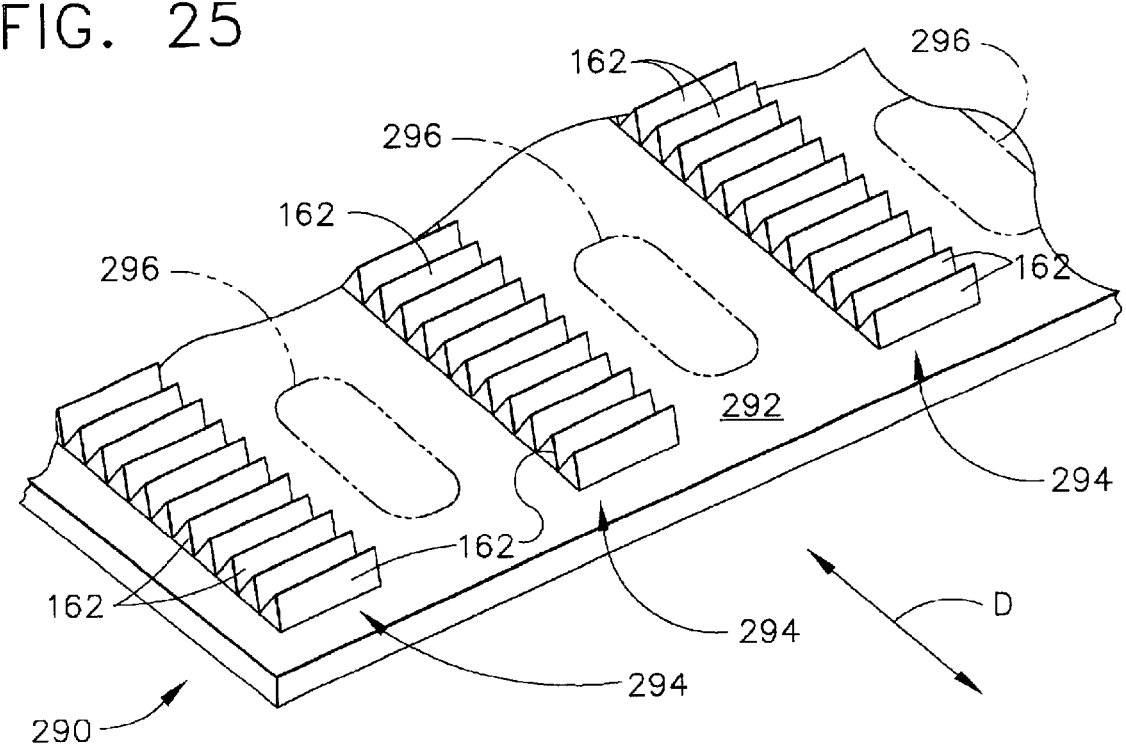
FIG. 26 is a perspective view of multiple arrays of elongated pyramidal-shaped microelements, as constructed according to the principles of the present invention.

FIG. 26 illustrates a similar arrangement of microelements, and includes multiple columns of pyramidal elongated microelements; its overall structure is designated by the reference numeral 290. The upper surface of the base or substrate 292 includes multiple columns 294 of elongated pyramidal microelements 162, in which there is no substantial space between each of the microelements 162 within a single column 294.

The individual columns 294 are spaced-apart from one another so that a planar area that is relatively open at the start is made available, at the areas designated by the reference numeral 296. These open areas 296 will receive the skin cells and other foreign substances on skin when the array/patch structure 290 is used to exfoliate the skin. In a preferred mode of use of the array/patch 290, the patch 290 will be placed upon skin and moved in a back and forth manner substantially in the direction of the arrow "D" (which is a preferred, predetermined direction).

Figure 27:
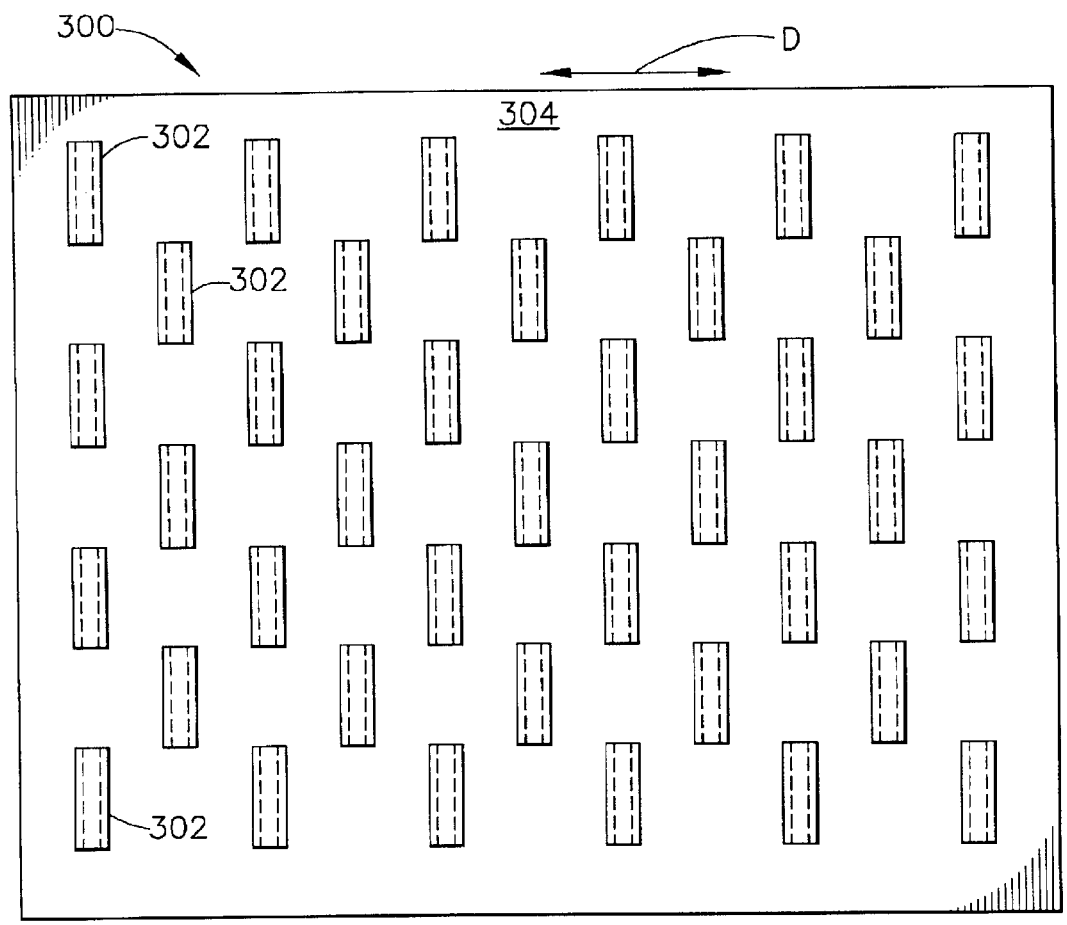
FIG. 27 is a plan view of an array of inverted wedge-shaped microelements, constructed as according to the principles of the present invention.

FIG. 27 illustrates an array of microelements, in which the array is generally designated by the reference numeral 300. The individual microelements 302 are arranged in columns on a substrate 304. The columns can have an offset of the microelements, as illustrated on FIG. 27. Alternatively, the individual columns of microelements 302 could be identical to one another, without any offset.

Figure 28:
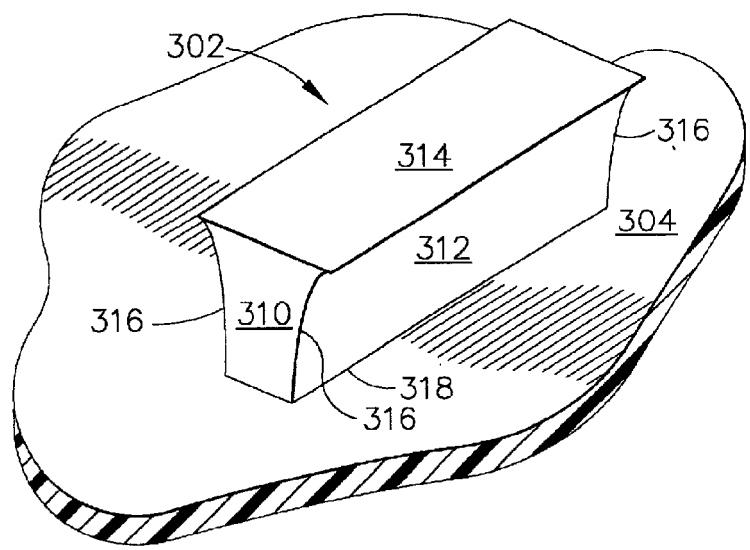
FIG. 28 is a perspective view of one of the inverted wedge-shaped microelements of FIG. 27.

FIG. 28 depicts one of the individual microelements 302 in greater detail. This microelement 302 has a shape that is something like an inverted curved wedge, or an inverted conical shape, as exhibited by one of its end walls 310. The curved edges of end wall 310 are depicted at 316, and a curved elongated side wall is depicted at 312. The top of the inverted wedge shape is depicted at 314, while the base line at 318 illustrates the point or line where the microelement 302 meets the substrate 304.

This inverted wedge shape is quite useful for exfoliation of skin, and can accumulate loose or dead skin cells and other foreign materials from the skin by use of a back and forth motion substantially along the line "D" (which is a preferred, predetermined direction). The height of the individual microelements 302 and the spacings therebetween will determine how much material will be removed from the skin surface.

Figure 29:
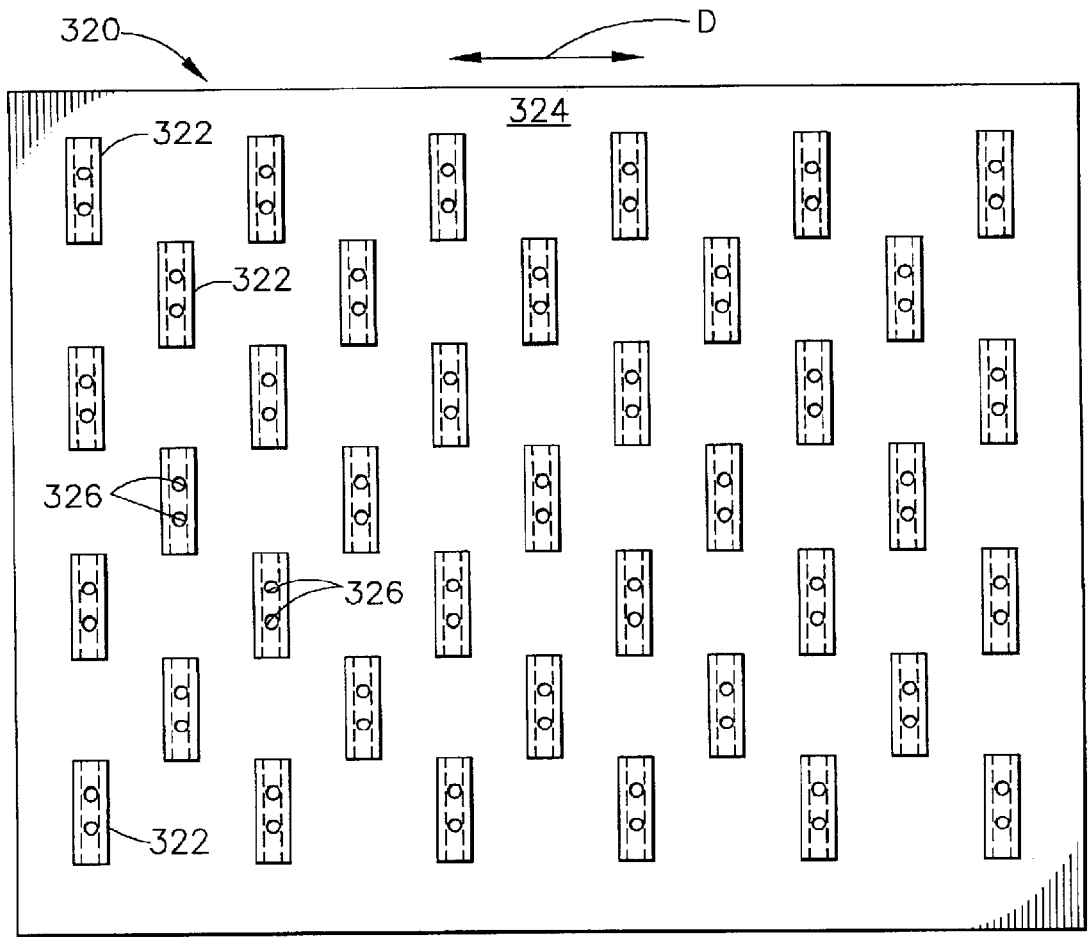
FIG. 29 is a plan view of an array of the inverted wedge-shaped microelements of FIG. 27 with the addition of through-holes in the microelements which penetrate through or into the substrate.

FIG. 29 illustrates an array 320 of similar inverted wedge-shaped microelements 322, which are mounted upon a substrate 324. In FIG. 29, the microelements 322 each include two through-holes 326, which are designed to pass one or more fluidic drugs or actives from one or more reservoirs to condition the skin after exfoliation.

Figure 30:
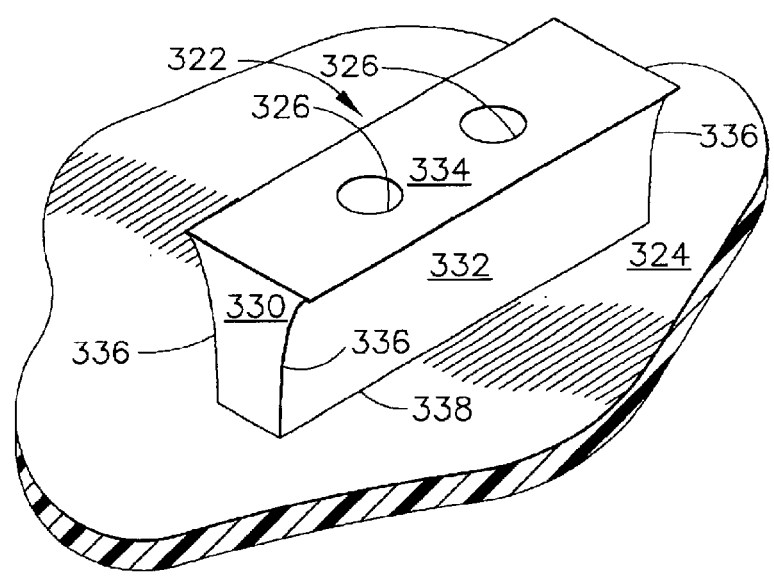
FIG. 30 is a perspective view of one of the inverted wedge-shaped microelements of FIG. 29.

FIG. 30 illustrates an individual inverted wedge microelement 322 in greater detail. The end wall 330 shows the overall shape of the inverted wedge (or inverted conical shape), which has two curved edges at 336 that adjoin the end wall 330 to adjacent elongated side walls 332. A top surface at 334 is illustrated as having the two through-holes 326, while a bottom base line 338 shows the line where the microelement 322 joins the substrate 324.

This inverted wedge-shaped microelement 322 can be used in a single operation for both exfoliation and for delivering at least one active to the skin surface. This active can be used to condition the skin just after many of the dead or loose skin cells have been removed.

Figure 31:
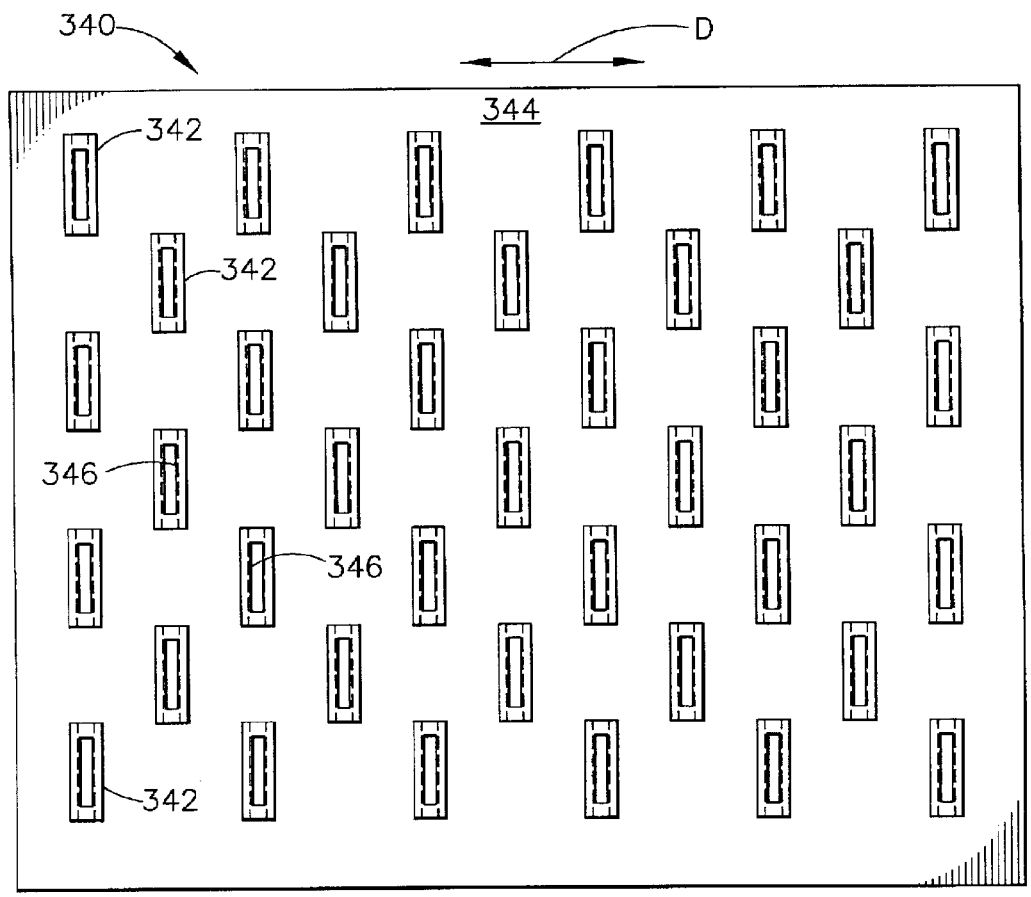
FIG. 31 is a plan view of an array of the inverted wedge-shaped microelements of FIG. 27 with the addition of through-slots in the microelements which penetrate through or into the substrate.
Figure 32:
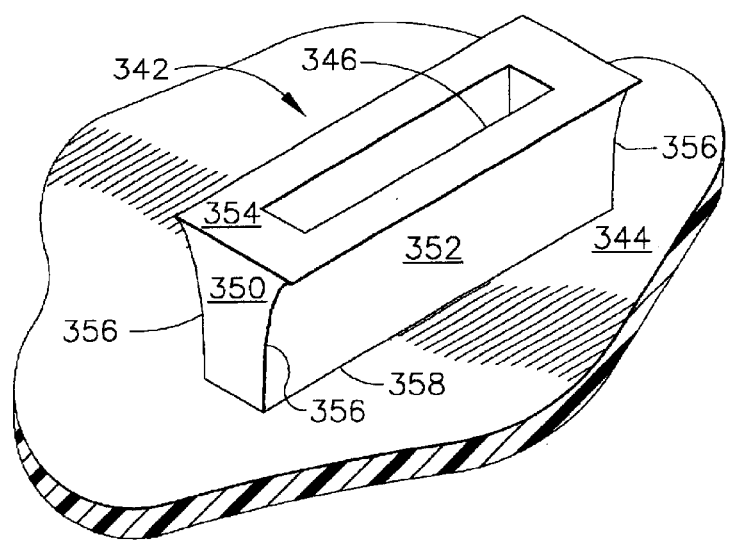
FIG. 32 is a perspective view of one of the inverted wedge-shaped microelements of FIG. 31.

An alternative structure for the inverted wedge microelement is illustrated in FIGS. 31 and 32. In FIG. 31, an array 340 of microelements 342 is depicted on a substrate 344. Each of the microelements 342 contains a through-slot 346, which can be seen in greater detail in the perspective view of FIG. 32.

In FIG. 32, the microelement 342 can be seen to have an inverted wedge shape (or inverted truncated conical shape) as exhibited by its end wall at 350. This end wall 350 is adjoined to adjacent elongated side walls 352 by curved edges 356. The top surface of the microelement is viewed at 354, while its bottom base line 358 illustrates the junction between the microelement 342 and the substrate 344.

The through-slot 346 can be used to deliver at least one active to skin, thereby making the array/patch 340 useable for both exfoliation and active delivery in a single operation. In a preferred mode of use, the array/patch 340 is placed on skin and then moved in a back and forth direction substantially along the line "D" (which is a preferred, predetermined direction).

Figure 33:
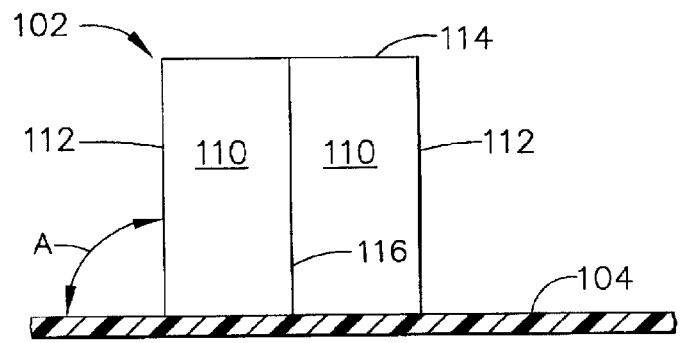
FIG. 33 is an elevational view in partial cross-section of a wedge-shaped microelement of FIG. 10, in which the side walls are perpendicular with respect to the substrate plane.

FIG. 33 illustrates the wedge-shaped microelement 102 from its "sharp" end in an elevational view. The two converging sides 110 are seen to form a relatively sharp edge at 116, which travels vertically from the top of the substrate/base 104 to the top surface 114 of the microelement 102. The angle "A" between the substrate top surface at 104 and the side wall 112 is clearly visible. On FIG. 33, this angle "A" is approximately 90°, and therefore forms a perpendicular angle.

Figure 34:
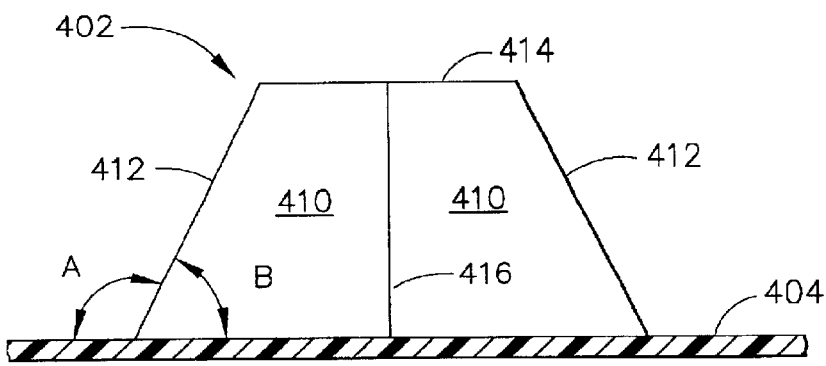
FIG. 34 is an elevational view in partial cross-section of a wedge-shaped microelement similar to that of FIG. 10, in which the side walls have an angular relationship that is not perpendicular with respect to the substrate plane.

FIG. 34 shows an alternative shape for a wedge-shaped microelement designated by the reference numeral 402. This wedge-shaped microelement has a similar appearance from above to that of the wedge-shaped microelement 102, except that its elongated side walls are not formed by a perpendicular angle to the substrate.

On FIG. 34, the substrate 404 is joined to the outer wall that is elongated along the side of the microelement (i.e., the wall 412) by an angle "A" that is greater than 90°. Its complimentary angle is illustrated at "B." Angle B is between 45° and 60° in FIG. 34, but of course could be any angle that will successfully operate to exfoliate the skin.

The front walls that converge are illustrated at 410, and converge along the relatively sharp edge at 416. This non-perpendicular wall shape of a microelement 402 may have some advantages with regard to manufacturing and with regard to overall strength of the structure.

Figure 35:
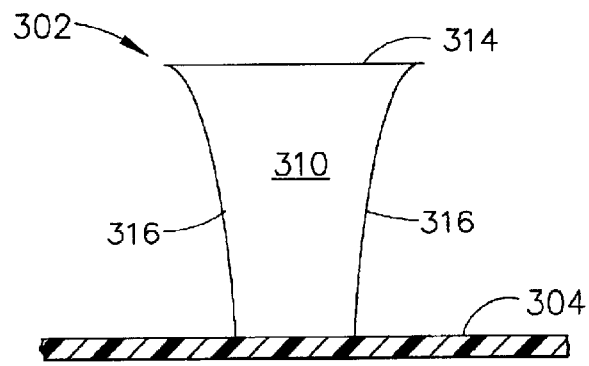
FIG. 35 is a side elevational view of an inverted wedge-shaped microelement of FIG. 28, in which the side walls are curved (i.e., concave).
Figure 36:
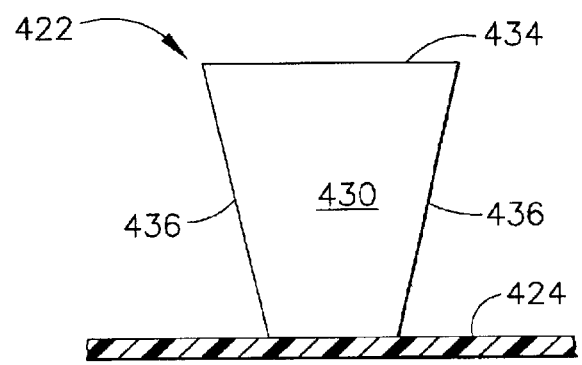
FIG. 36 is a side elevational view of an inverted wedge-shaped microelement similar to that of FIG. 28, in which the side walls are straight (i.e., flat).

FIG. 35 illustrates an end view of the inverted wedge or inverted truncated cone-shaped microelement 302. As can be seen, the side walls 316 are clearly curved in a concave manner. This is in contrast to the structure illustrated in FIG. 36, in which the microelement 422 has straight side walls 436. A similar top surface 434 exists as compared to the top 314 in FIG. 35. The overall shape of the end surface 430 is fairly similar to that of the end surface 310, but of course the shape in FIG. 36 is that of a truncated cone. The base/substrate is shown at 424.

Figure 37:
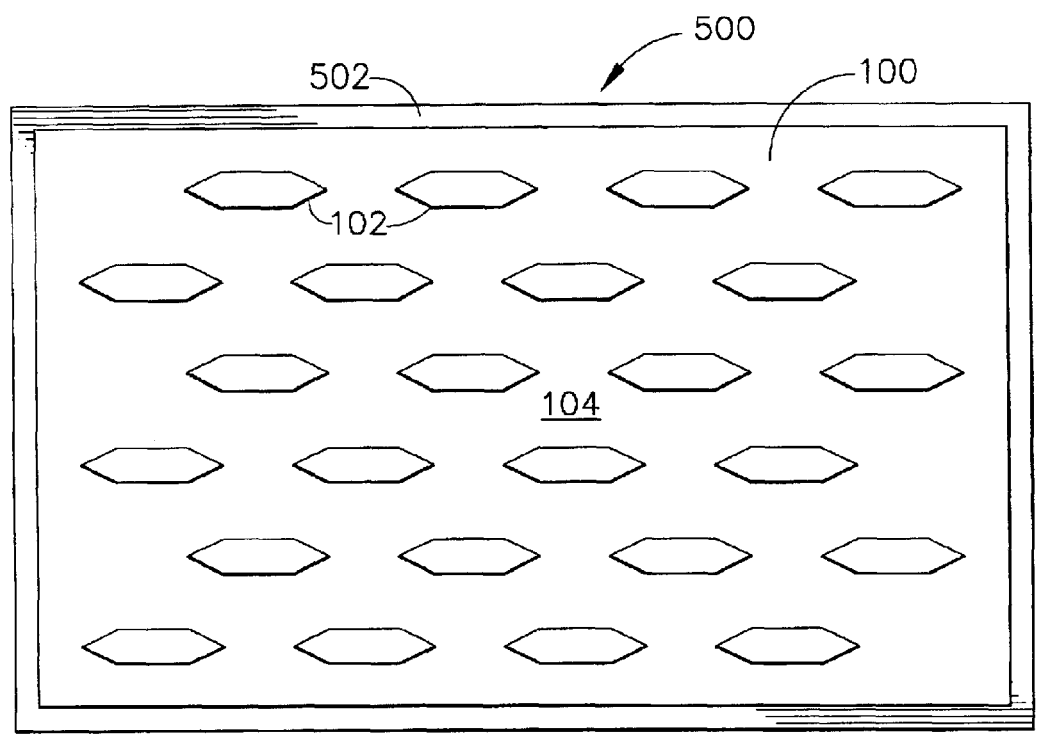
FIG. 37 is a plan view of a microelement array as seen in FIG. 10, with the addition of a non-woven backing material that is laminated to the original substrate.

FIG. 37 illustrates an array of wedge-shaped microelements 102 on a substrate 104 that makes up a microstructure apparatus designated by the reference numeral 100. Microstructure apparatus 100 comprises a top layer that is laminated to a non-woven backing 502, which is preferably thin enough so as to be substantially flexible. This overall structure is generally designated by the reference numeral 500 on FIG. 37.

The top layer 100 that contains the multiple microelements 102 can have as a substrate and microelement material some type of moldable plastic, such as nylon, or a polycarbide material, or PMMA, for example (and these materials may be used with any microelement shape). The bottom or backing material 502 preferably is a substantially flexible material that exhibits a soft texture. Typically a non-woven material gives an impression of cloth, and thus can provide the desired soft texture.

The non-woven backing material 502 can be laminated with the microelement layer 100 by use of a chemical glue or a heat-activated adhesive, for example. On FIG. 37, the non-woven backing is somewhat larger in length and width than the microelement layer 100, and thus can be seen along the edges.

Figure 38:
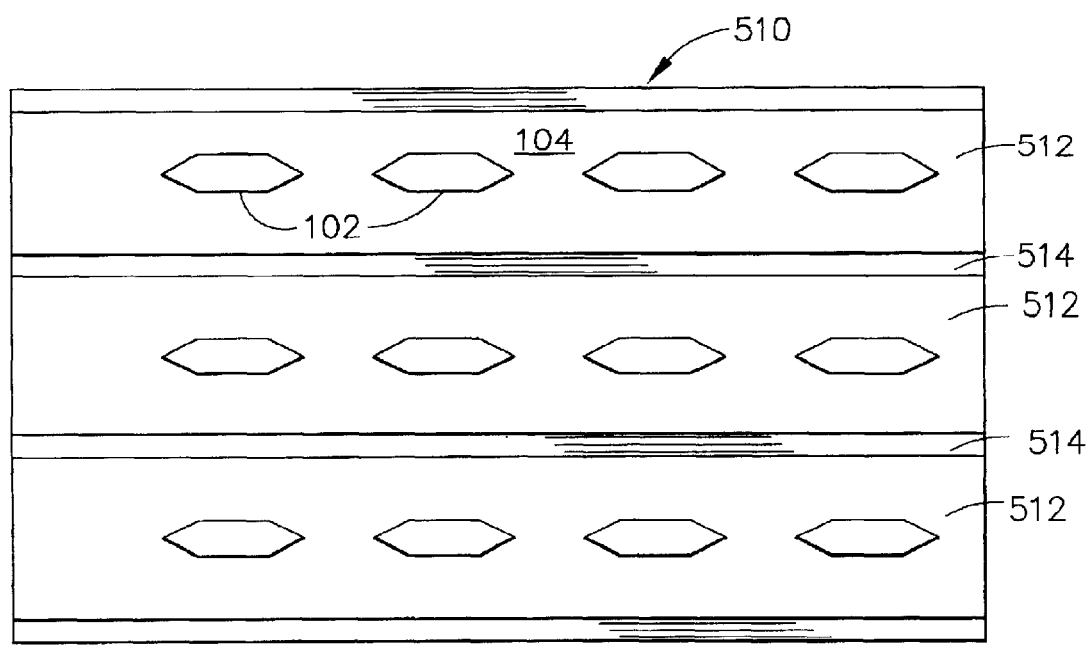
FIG. 38 is a plan view of a plurality of microelement strips that are laminated onto a non-woven backing.

FIG. 38 illustrates a similar laminated structure, however, the microelements 102 are formed as strips 512, in which there are several such strips that contain rows of the microelements. The non-woven backing material can be seen both along the top and bottom edges, and also between the strips at 514 on FIG. 38. The overall structure is generally designated by the reference numeral 510.

Figure 39:
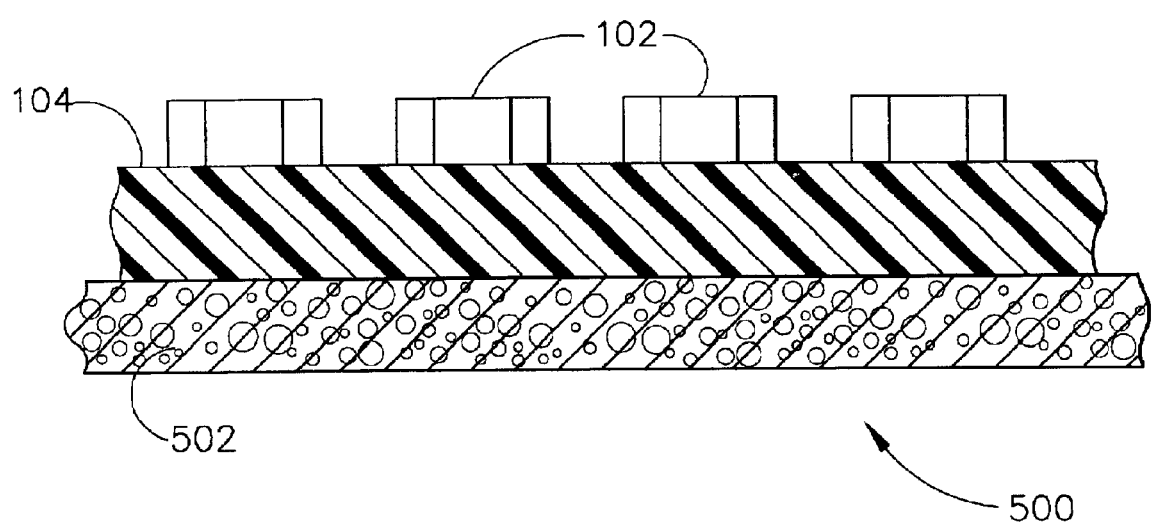
FIG. 39 is an elevational view in partial cross-section of a microelement array as seen in FIG. 10, showing further details of the substrate and non-woven backing.

In FIG. 39, the microelements 102 are visible at the top, as residing above the substrate 104. The bottom portion of the substrate is permanently affixed to the non-woven backing material 502, thus leading to the overall structure at 500.

As discussed above, the fixing of the non-woven backing material 502 to the substrate 104 can be by some type of adhesive used in lamination, or perhaps using a sonic bonding process. Alternatively, a co-extruded material could be used.

One major advantage to using a non-woven backing material as depicted in FIGS. 37–39 is that this non-woven material 502 (or 514 on FIG. 38) can be impregnated with at least one active, and thereby effectively become a "reservoir" without creating an actual chamber having an open volumetric space. This not only saves a manufacturing procedure step by not requiring a true open chamber to be constructed, but also allows the overall structure of the "patch" shown in the earlier figures to be made of a substantially flexible material that is much less likely to exhibit breakage problems.

It will be understood that various shapes of microelements can be used with the non-woven backing material, and various shapes of substrates can be laminated or otherwise affixed to the non-woven backing material. It will also be understood that the backing material may or may not be impregnated, all without departing from the principles of the present invention. Finally, it will also be understood that other suitable materials besides non-woven materials could be used for the backing at 502 and 514 on FIGS. 37 and 38, all without departing from the principles of the present invention.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

What is claimed is:

1. A method for removing cells from skin, said method comprising:
   (a) providing a microstructure having a substrate and a plurality of microelements;
   (b) placing said microstructure on skin then rubbing the microstructure against said skin, and along the surface of the skin, thereby scraping and accumulating skin cells on said substrate in areas between said plurality of microelements; and
   (c) withdrawing said microstructure from said skin, and thereby removing a large majority of said skin cells that have accumulated upon said substrate;

said method further comprising the steps of:

providing a fluidic compound that flows through first passageways in said substrate, then along channels in walls of said microelements and through second passageways in said microelements, thereby both exfoliating said skin and delivering said fluidic compound to said skin in a single procedure.

2. The method as recited in claim 1, wherein a shape of at least some of said plurality of microelements and their adjacent substrate comprises one of:

(a) a pyramid having at least one channel along a wall of said pyramid, and at least one passageway in said substrate proximal to the wall of said pyramid, said channel being in fluidic communication with said passageway; or (b) an open, topless box having three walls, and at least one passageway in said substrate proximal to one of said three walls; or (c) a wedge having at least one passageway therethrough which is in fluidic communication with at least one other passageway in said substrate; or (d) an elongated triangle having at least one channel along a wall of said elongated triangle, and at least one passageway in said substrate proximal to the wall of said elongated triangle, said channel being in fluidic communication with said passageway; or (e) an inverted wedge with curved side walls having at least one passageway therethrough which is in fluidic communication with at least one other passageway in said substrate; or (f) an inverted wedge with substantially flat side walls having at least one passageway therethrough which is in fluidic communication with at least one other passageway in said substrate.

3. The method as recited in claim 2, further comprising: (a) providing at least one chamber that holds said fluidic compound on a distal side of said substrate, wherein said distal side is opposite of a proximal side of said substrate upon which said microelements are formed; and (b) delivering at least one said fluidic compound from said chamber through said at least one passageway in said substrate onto said skin.

4. The method as recited in claim 1, further comprising: after said step of withdrawing the microstructure from the skin, manually applying a fluidic compound to substantially a same area of said skin.

5. The method as recited in claim 1, further comprising: providing a fluidic compound on a same surface of said microstructure which contains said microelements, wherein said fluidic compound is at least in part applied to substantially a same area of said skin during said rubbing step.

* * * * *

UNITED STATES PATENT AND TRADEMARK OFFICE
CERTIFICATE OF CORRECTION

PATENT NO. : 6,821,281 B2
DATED : November 23, 2004
INVENTOR(S) : Sherman et al.

It is certified that error appears in the above-identified patent and that said Letters Patent is hereby corrected as shown below:

Column 11,
Line 50, delete "exfoliate" and insert therefor -- exfoliated --.

Column 15,
Line 56, delete "though" and insert therefor -- through --.
Line 58, delete "passgeway" and insert therefor -- passageway --.

Signed and Sealed this

Seventh Day of June, 2005

JON W. DUDAS
*Director of the United States Patent and Trademark Office*